United States Patent
Zhu et al.

(10) Patent No.: US 8,623,919 B2
(45) Date of Patent: Jan. 7, 2014

(54) METHOD OF SYNTHESIZING S-ALLYL-CYSTEINE ANALOGUES AND THEIR THERAPEUTIC APPLICATION IN TREATING MYOCARDIAL INFARCTION

(75) Inventors: Yizhun Zhu, Singapore (SG); Qian Wang, Shanghai (CN); Yichun Zhu, Shanghai (CN); Qing Mu, Shanghai (CN)

(73) Assignee: Fudan University, Shanghai (CN)

( * ) Notice: Subject to any disclaimer, the term of this patent is extended or adjusted under 35 U.S.C. 154(b) by 508 days.

(21) Appl. No.: 12/185,056

(22) Filed: Aug. 1, 2008

(65) Prior Publication Data

US 2009/0036534 A1 Feb. 5, 2009

(30) Foreign Application Priority Data

Aug. 2, 2007 (CN) .......................... 2007 1 0044525

(51) Int. Cl.
*A01N 37/12* (2006.01)
*A01N 37/44* (2006.01)
*A61K 31/195* (2006.01)

(52) U.S. Cl.
USPC .......................................... 514/562; 560/153

(58) Field of Classification Search
None
See application file for complete search history.

(56) References Cited

U.S. PATENT DOCUMENTS 3,892,852 A * 7/1975 Joullie et al. .................... 514/62

OTHER PUBLICATIONS

Banerjee et al. "Chronic oral administration of raw garlic protects against isopreterenol-induced myocardial necrosis in rat", Comparative Biochemistry and Physiology Part C, vol. 136, 2003, pp. 377-386.*
Kodera et al. Garlic chemistry:chemical and biological properties of sulfur-containing compounds derived from garlic, American Chemical Society, pp. 346-357, Chapter 30, 2003.*
Sardao et al. "Vital imaging of H9c2 myoblasts exposed to tert-butylhydrogenperoxide-characterization of morphological features of cell death", BMC cell biology, vol. 8, No. 11, Mar. 16, 2007.*
Aggarwal et al "Suppression of nuclear factor-kappa B activation pathway by spice-derived phytochemicals", Ann N Y Acad Sci. 2004, vol. 1030 pp. 434-441.*
Borek "Antioxidant health effects of aged garlic extract", American Society for Nutritional Sciences, vol. 131, pp. 1010S-1015S, 2001.*
Padmanabhan et al, Toxicoloy 224 (2006) 128-137.*
Lefer, PNAS, Nov. 13, 2007, vol. 104, No. 46, 17907-17908.*
Li et al, Hydrogen sulfide is a novel mediator of lipopolysaccharide-induce inflammation in the mouse, FASEB, Apr. 29, 2005.*
Wattanapitayakul et al, Basic & Clinical Pharmacology & Toxicology 2005, 96, 80-87.*
Hamid et al, Toxicology in vitro 18 (2004) 703-710.*
Singh et al, Am. J. Cariol. 1996, 77:232-236.*

* cited by examiner

*Primary Examiner* — Brandon Fetterolf
*Assistant Examiner* — Jean Cornet
(74) *Attorney, Agent, or Firm* — Yuan Qing Jiang

(57) ABSTRACT

A pharmaceutical composition and methods of producing and application of the composition for treating myocardial infarction of a subject are disclosed. The pharmaceutical composition comprises a therapeutically effective amount of at least one synthesized compound selected from the group consisting of SEC, SPC, SBC, SPEC, SAC, SAMC, and SPRC, and a pharmaceutically acceptable carrier.

3 Claims, 17 Drawing Sheets

METHOD OF SYNTHESIZING S-ALLYL-CYSTEINE ANALOGUES AND THEIR THERAPEUTIC APPLICATION IN TREATING MYOCARDIAL INFARCTION

FIELD OF INVENTION

The present invention relates to methods of synthesizing S-allyl-cysteine analogues and their therapeutic composition and applications in treating myocardial infarction.

BACKGROUND OF INVENTION

Myocardial infarction is irreversible necrosis of heart muscle cells caused by ischemic heart disease, which is characterized by coronary blood flow diminished to the level unsustainable to the metabolic demand of myocardium.

Common symptoms of ischemic heart disease include angina, shortness of breath, or fatigue. Often angina is worsened if the patient exerts after a meal, or walks into a cold weather, or suffers from emotional stress.

The major pathogenesis of myocardial infarction is coronary artery stenosis, leading to myocardial cells starved for oxygen (hypoxia) and glucose, the result of which is death or permanent damage of myocardial cells (myocytes).

The etiologies for coronary artery stenosis are fixed atherosclerotic obstruction, acute plaque rupture, coronary artery thrombosis, and vasospasm. In order to study myocardial infarction, lab models are established by occlusive ligature of coronary artery of experimental animals to reproduce ischemia caused by coronary artery stenosis, or by deprivation oxygen (hypoxia) and glucose supply to cultured myocardial cells.

Morphologically the area of necrotic myocardium corresponds to the area where occluded coronary artery supplies. The myocardial tissue affected turns from pallor to cyanotic, further to softened yellow central area with a hyperemic rim. Eventually the dead myocardial tissue is replaced by a fibrotic white thin scar. The severity of the damage to myocardium is proportional to the area affected by coronary artery stenosis and the time duration of ischemia.

Under microscope the ischemic myocardial cells display various morphological changes ranging from myocytolysis, eosinophilic cell infiltration with intercellular edema of the myocardium, acute inflammation of the myocytes, macrophages removing dead myocytes, granulation tissue, to scar tissue.

Biochemical lab diagnosis provides specific, sensitive and timely results indicating myocardial cell stress, injury, and death. The lab test markers relevant to myocardial muscle cell's current biomedical conditions are creatine kinase subfraction MB (CK-MB) level, cardiac troponin levels (troponin-T and troponin-I), Lactate Dehydrogenase (LDH) level and myoglobin level.

Elevation of CK-MB indicates acute myocardial cell injury, since it is a specific enzyme in myocardial cells and a good marker of injury of myocardial cells. Isoforms 1 and 2 of CK-MB can also be tested, and the ratio of the two CK-MB isoforms can provide further information about the injury condition of myocardial cell.

Troponin-T and Troponin-I are proteins in myocardial cells. Elevation of the Troponin-T and Troponin-I indicate that myocardial cells are injured.

Elevation of LDH level is another indicator of myocardial infarction.

Myoglobin is structure protein of myocytes. Increase of its level indicates myocardial infarction.

Numerous drug treatments to combat coronary heart disease have been developed. Commonly prescribed drugs to treat coronary diseases are beta-blockers, nitrates, calcium channel blockers, angiotensin-converting enzyme (ACE) inhibitors, and antiplatelet coaggregation drugs.

Beta-blockers are prescribed to alleviate the effect of adrenaline and noradrenaline on the heart. Nitroglycerin dilates coronary blood vessels instantly. Calcium channel blockers prevent blood vessels from constricting and counter coronary artery spasm. ACE inhibitors, such as ramipril reduce the risk of heart attack. Antiplatelet coaggregation drugs, such as aspirin reduce the aggregation of platelets so that they do not clump and stick on blood vessel walls. Some of the drugs are used in combination to prevent or reduce ischemia and to minimize symptoms.

Searching for new drugs to treat coronary heart disease has been an on going effort worldwide. Natural resources have been the dependable sources for new drug development for long time. New drugs developed from substances originated from plants are believed less dependent forming, with fewer side effects.

SUMMARY OF THE INVENTION

The present invention provides new pharmaceutical compositions and methods of production and application of the pharmaceutical compositions to treat myocardial infarction.

In one embodiment, provided is a pharmaceutical composition for treating myocardial infarction in a subject comprising a therapeutically effective amount of at least one synthesized compound selected from the group consisting of SEC, SPC, SBC, SPEC, SAC, SAMC, and SPRC, and a pharmaceutically acceptable carrier.

In another embodiment, provided is a method of treating myocardial infarction comprising administering a subject the pharmaceutical composition of a therapeutically effective amount of at least one synthesized compound selected from the group consisting of SEC, SPC, SBC, SPEC, SAC, SAMC, and SPRC, and a pharmaceutically acceptable carrier to induce at least one biochemical change in ischemic cardiac muscle cells to improve the ischemic cardiac muscle cells survive rate, reduce LDH leakage from the ischemic cardiac muscle cells, and reduce infarction area of myocardial infarction in the subject.

In yet another embodiment, provided is a method for synthesizing SPRC comprising preparing an $NH_4OH$ solution containing cysteine by dissolving cysteine hydrochloride in said solution, admixing organic bromine with said solution, synthesizing SPRC in the mixture solution by stirring said solution, extracting SPRC by filtration, purifying SPRC by recrystallisation, and determining SPRC by Proton Nuclear Magnetic Resonance Spectroscopy.

Other features and advantages of the invention will be apparent from the following detailed description, and from the claims.

DETAILED DESCRIPTION OF THE INVENTION

Figure 1:
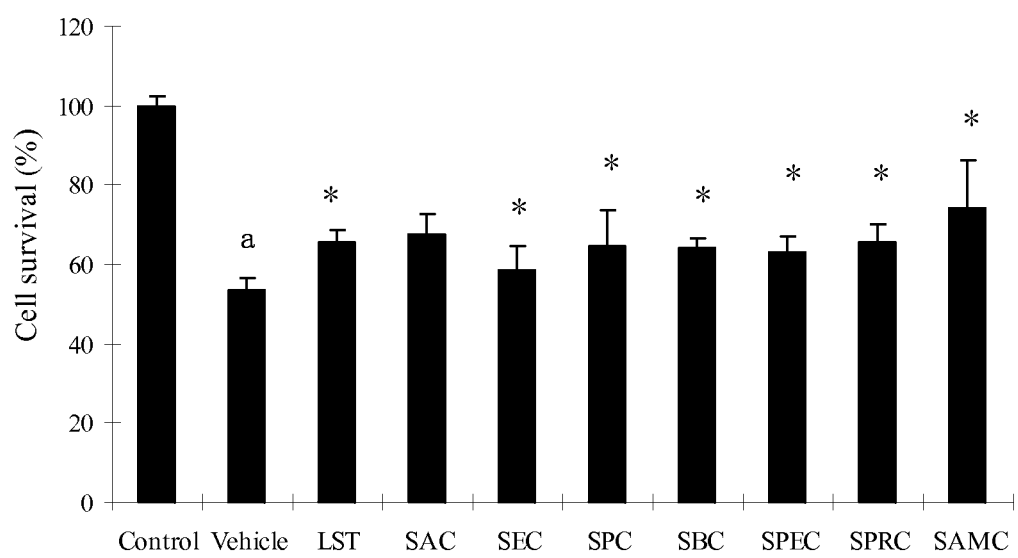
FIG. 1 shows effects of SAC and analogues on survive rate of myocardial cells under hypoxia/reoxygenation condition.

Garlic (*Allium sativum*) has been used as both foodstuff and medicine for thousands of years. In some cultures, such as Egypt, Greece, Rome, Northern Europe, and China, it is believed in folklores that dietary consumption of garlic can keep people healthy. Some people believe that eating garlic helps suppressing the development of certain diseases such as cancer, common cold and infection.

Various researches have been conducted to study the chemical compositions of garlic and their medicinal use. Some studies are focused on aged garlic extract (AGE), which is produced by aging and extracting organic fresh garlic in water at room temperature for 20 months. The resulting aged garlic extract is high in water-soluble phytochemicals, including cysteine derivatives such as S-allyl cysteine (SAC), S-allyl mercaptocysteine (SAMC) and S-methyl cysteine, and gamma-glutamyl cysteine derivatives. The process increases AGE's phytochemical levels, which is believed to have antioxidant effect and is largely responsible for benefiting human health. Water-soluble cysteine derivatives from AGE are odorless, more chemically stable and safer for human consumption.

A number of cysteine derivatives from AGE have been isolated, and their chemical structures have been determined. For example, S-allyl cysteine (SAC), and its analogous of S-ethyl cysteine (SEC), S-propyl cysteine (SPC), S-butyl cysteine (SBC), S-pentyl-L-cysteine (SPEC), S-allylmercapto cysteine (SAMC), S-propargyl-cysteine (SPRC) are a few phytochemicals that researchers are interested in:

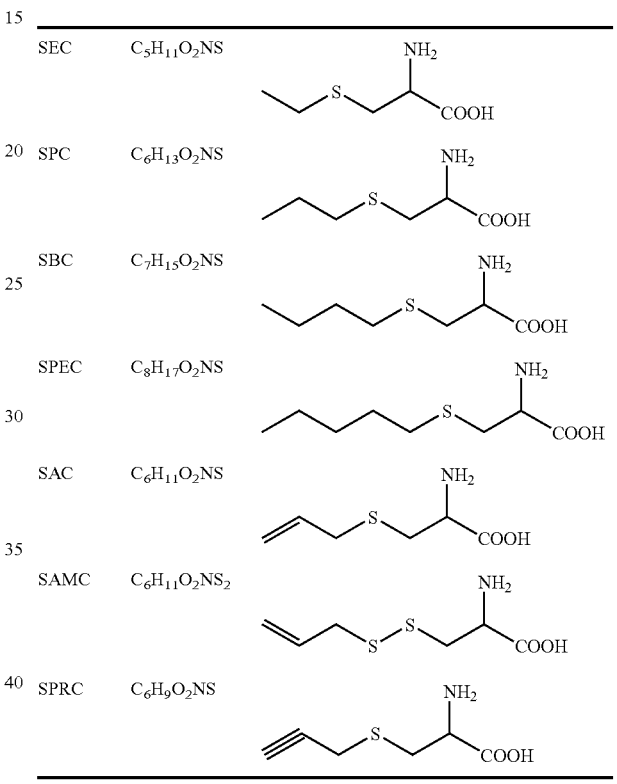

The research results revealed that the purified phytochemicals have a wide range of health benefits and medicinal applications. Many of the purified phytochemicals have the same antioxidant effects of AGE in the studies. More biomedical researches disclosed further medicinal applications of the purified phytochemicals. For example, SAC, SEC and SPC inhibit cholesterol synthesis by deactivating HMG-CoA reductase (J. Nutr. 132:1129-1134, 2002). Five cysteines from aged garlic extract, N-acetyl cysteine (NAC), SAC, SEC, SMC, and SPC, are able to treat hyperlipidemia development in mice consuming a high saturated fat diet (Lipids, 2004, Vol. 39, No. 9, pp. 843-848).

WO/2001/035972 disclosed a method using a composition containing S-allyl cysteine and S-allyl mercapto cysteine from aged garlic extract with vitamin C and vitamin E for treating sickle cell disease.

Another research report disclosed that SAC is used for treating cerebral ischemic injury of neurons due to its antioxidant activity (Free Radical Research, Volume 40, Issue 8 Aug. 2006, pages 827-835).

Yet another research report disclosed that dietary SAC reduces mortality with decreased stroke in stroke-prone spontaneously hypertensive rats (Biosci Biotechnol Biochem., Vol. 70; No. 8; Page. 1969-1971 (J-STAGE)(2006)).

SAC is a representative sulfur containing cysteine which can be derived from S-Alk(en)yl cysteine sulfoxides (ACSs) degradation. Previous reports have shown that SAC has anti-oxidant, anti-cancer and anti-hepatotoxic effects. S-propargyl-cysteine (SPRC) is a structural analogue of S-allylcysteine (SAC). It is anticipated that the analogue SPRC has better antioxidant activity in that the SPRC structure is similar to that of SAC's, besides, SPRC has better selectivity to interact with the enzyme cystathionine-γ-lyase (CSE).

Interestingly, both SPRC and SAC are found to increase hydrogen sulfide ($H_2S$) production in cells and induce the enzyme cystathionine-γ-lyase (CSE) at both the transcriptional and protein level. These results suggest that SPRC and SAC offer their antioxidant effects via a $H_2S$ mediated pathways. In addition, SPRC represents a pharmacological agent that can be used to modulate endogenous $H_2S$ levels in cells. SPRC deserves further studies to assess its effectiveness for ischemic heart diseases.

However, there is no report that SAC and its analogous of SEC, SPC, SBC, SPEC, SAMC, SPRC can be applied to treat myocardial infarction thus far.

Furthermore, the process to obtain phytochemicals such as SAC and analogues from natural resources is complicate and lengthy, involving at least growing the plants, harvesting the plants, extracting the phytochemicals from the plants, isolating and purificating the phytochemicals. Apparently the process to obtain SAC and analogues from natural resources costs time and money, let alone its impact on the environment.

Therefore, it is necessary to develop some chemical methods to synthesize SAC and analogues, and explore the medicinal application of the SAC and analogues in treating myocardial infarction.

In one embodiment according to the present invention, SAC and its analogous of SEC, SPC, SBC, SPEC, SAMC, SPRC are artificially synthesized.

The methods to synthesize SAC and its analogous are disclosed as following:

A solution containing cysteine by dissolving cysteine hydrochloride in an aqueous solution is prepared. For synthesizing SAC, SPC, SBC, SPEC and SPRC the solution is an alkaline solution, preferably a pre-cooled cysteine $NH_4OH$ solution. For synthesizing SAC, 3-bromopropene is added into a pre-cooled cysteine $NH_4OH$ solution. For synthesizing SEC, ethyl bromide is added into an aqueous solution containing cysteine at room temperature, with its pH adjusted to 9.5-10 by adding ammonia water. For synthesizing SPC, propyl bromide is added into a pre-cooled cysteine $NH_4OH$ solution. For synthesizing SBC, butyl bromide is added into a cysteine $NH_4OH$ ethanol solution in 25 degree C. For synthesizing SPEC, pentyl bromide is added into a cysteine $NH_4OH$ ethanol solution in 25 degree C. For synthesizing SAMC, allicin is added in small portions into an aqueous solution containing cysteine under vigorous stirring at room temperature. For synthesizing SPRC, propargyl bromide is added to the ice-cooled solution of L-cysteine hydrochloride in $NH_4OH$. In order to synthesize corresponding SAC analogues the mixture solutions are stirred vigorously so that the organic bromines react with corresponding cysteine solutions. The synthesized SAC and analogues are extracted by filtration, and the filtered products are concentrated in vacuum, washed in water or ethanol or ethyl ether several times. The chemical structures of purified SAC analogues are determined by Proton Nuclear Magnetic Resonance Spectroscopy.

Various SAC analogues may be made from cysteine using a range of chemistries, or from other chemical synthesis. Additionally derivations will be recognized and are routine to those of skilled in the art.

In another embodiment, provided is a pharmaceutical composition for treating myocardial infarction in a subject comprising a therapeutically effective amount of at least one synthesized compound selected from the group consisting of SEC, SPC, SBC, SPEC, SAC, SAMC, and SPRC, and a pharmaceutically acceptable carrier.

The structures of SAC analogues are capable of forming pharmaceutically acceptable salts, including acid addition salts and base salts, as well as solvates, such as hydrates and alcoholates. All of these pharmaceutical forms are contemplated by this invention and are included herein.

Pharmaceutically acceptable acid addition salts of the composition of SAC analogues include salts derived from inorganic acids such as hydrochloric, nitric, phosphoric, sulfuric, hydrobromic, hydriodic, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like.

The phrase "pharmaceutically acceptable" is employed herein to refer to compositions and dosage forms suitable for use in contact with the tissues of human beings and animals without excessive toxicity, irritation, allergic response, or other problem or complication, commensurate with a reasonable benefit versus risk ratio.

The synthesized SAC analogues of the invention may be formulated into pharmaceutical compositions by admixture with pharmaceutically acceptable non-toxic excipients or carriers. Common excipients or carriers may be sterile water or saline, polyalkylene glycols such as polyethylene glycol, oils from vegetable origin, hydrogenated naphtalenes etc. Such compounds or compositions may be prepared for parenteral administration intravenously, subcutaneously, and intramuscularly, particularly in the form of liquid solutions or suspensions in aqueous physiological buffer solutions; for oral administration, particularly in the form of tablets or capsules; or for intranasal administration, particularly in the form of powders, nasal drops, or aerosols. Sustained release compositions are also encompassed by the present invention. Other suitable administering systems include ethylene-vinyl acetate copolymer particles, osmotic pumps, implantable infusion systems, and liposomes. Compositions for other routes of administration may be prepared as desired using standard methods.

In an alternate embodiment, the invention relates to compositions and kits comprising a first therapeutic agent including SAC analogues thereof and at least one of second therapeutic agent. The second therapeutic agent is not SAC or its analogues thereof. These compositions or kits are effective to treat myocardial infarction in a subject. Various therapeutic agents, including beta-blockers, nitrates, calcium channel blockers, angiotensin-converting enzyme (ACE) inhibitors, and antiplatelet coaggregation drugs may be used in the composition.

The effectiveness of SAC and its analogues on treating myocardial infarction is determined in both cultured myocardial cells and animal models.

Myocardial cells are deprived from oxygen and glucose for 6 hours, which is a conventional model for ischemic myocardial infarction. The hypoxic myocardial cells are then reperfused with normal amount of oxygen and glucose (hypoxia/reoxygenation process). Several groups of myocardial cells are administered with SAC and its analogues respectively 12 h before hypoxic injury. During hypoxia/reoxygenation process, with one group of hypoxic cells left untreated (No SAC analogues are administered.) as a model control of hypoxia/reoxygenation (Vehicle group) and one normoxic control group of myocardial cells cultured without hypoxia/reoxygenation process (Control group, with normal oxygen supply). The effects of SAC and its analogues inducing biochemical changes in the hypoxic myocardial cells, the survival rate of the hypoxic myocardial cells and the LDH leaking from the ischemic myocardial cells are observed. The results indicate that endogenous $H_2S$ level in the hypoxic myocardial cells is elevated by the SAC analogues treatments. Endogenous $H_2S$ contributes to the cardioprotection by metabolic inhibition preconditioning in the rat ventricular myocytes (Journal of Molecular and Cellular Cardiology, Vol. 40, Issue 1, January 2006, Pages 119-130).

Several biochemical markers are assessed to determine the effects of SAC analogues. In hypoxic myocardial cells treated with SAC analogues, LDH leakage (release) from the cells is reduced. The effect of SAC analogues on reducing LDH leakage from hypoxic cells can be reversed by PAG (DL-propargylglycine, a cystathionine gamma-lyase (CSE) inhibitor inhibiting endogenous $H_2S$ production). The result indicates that the reduction of LDH leaking rates in SAC and analogue treated cells are correlated with the survival rate of myocardial cell under hypoxia/reoxygenation condition, and is mediated by endogenous $H_2S$ in the injured myocardial cells.

The activities of SOD (superoxide dismutase) in SAC analogues treated hypoxic cells are elevated. The effect of SAC analogues on elevating SOD activity from hypoxic cells can be reversed by PAG. The result indicates that the elevating SOD activity in SAC analogue treated cells are correlated with the survival rate of myocardial cell under hypoxia/reoxygenation condition, and is mediated by endogenous $H_2S$ in the injured myocardial cells. SOD subtype studies further reveal that the analogues SPC, SBC and SPEC, which have saturated carbon chain in their molecular structures, are able to elevate the activities of Cu—Zn SOD in cytoplasm in myocardial cell under hypoxia/reoxygenation condition. PAG also reverses the effect on elevating SOD activity of SPC, SBC and SPEC. Analogues SPRC and SEC are able to elevate Mn-SOD activity in mitochondria in myocardial cell under hypoxia/reoxygenation condition. PAG also reverses the effect.

Catalase activity in SAC analogues treated hypoxic cells groups is elevated.

Lipid peroxidations in hypoxic cells treated with SAC analogues SEC, SPC, SPRC were inhibited by SAC analogues. SAC analogues can significantly inhibit oxygen free radicals in the cells, thereby inhibiting lipid peroxidation in hypoxic myocardial cells, reducing the level of MDA (malondialdehyde), which is a product of lipid peroxidation. The inhibition effect on lipid peroxidation could be reversed by PAG.

SAC analogues can inhibit myocardial cell apoptosis, and have great value in application of treating heart disease.

Similar experiments are done on cultured H9c2 cardiac muscle cells groups with the same experiment condition and different dosages of SPRC treatments. The results of the experiments confirm that endogenous $H_2S$ level in $H_2O_2$ injured H9c2 cells is elevated by SPRC treatments. The activities of SOD (superoxide dismutase) and catalase are elevated in $H_2O_2$ injured H9c2 cells, SPRC can significantly inhibit oxygen free radicals in the cells, thereby inhibiting lipid peroxidation in $H_2O_2$ injured H9c2 cells, reducing the level of MDA (malondialdehyde), which is a product of lipid peroxidation. It is also observed that the apoptosis of hypoxic myocardial cells is decreased, the survival rate of the in $H_2O_2$ injured H9c2 cells is increased and the LDH releasing from the in $H_2O_2$ injured H9c2 cells are reduced by three dosages of SPRC treatment. The results indicate that the effects of SPRC is concentration dependent.

Animal model for myocardial infarction is employed and effectiveness of SAC analogues in treating MI is tested.

Rats are randomly assigned to 4 experiment groups: Sham operated on and treated with saline group (Sham group, negative control), sham operated on and treated with SPRC and SAC groups (Sham+SPRC and Sham+SAC), ligation operated on and treated with saline group (MI group, model control), ligation operated on and treated with SPRC and SAC groups (MI+SPRC and MI+SAC). Rats in SPRC and SAC groups are pre treated with SPRC and SAC respectively for 7 days.

Rats are operated on and MI is induced according to correspondent experiment groups by ligating the left anterior descending coronary artery at approximately 2-3 mm from its origin. The MI model is established when the area of myocardium supplied by the ligated coronary artery turns to pallor, and ECG recording shows the ST segment is elevated. Then the rats are given water and food, returned to their cages according to experiment groups. SPRC and SAC treatment groups are given SPRC and SAC continuously for 2 more days.

Forty eight hours after the surgery, ECG is recorded for each rat in each group. Blood samples are taken from abdominal aorta from each rat in each group. Then the rats are sacrificed and their hearts are taken. The heart tissues from the rats are stained and the myocardial infarction areas are observed.

Figure 12:
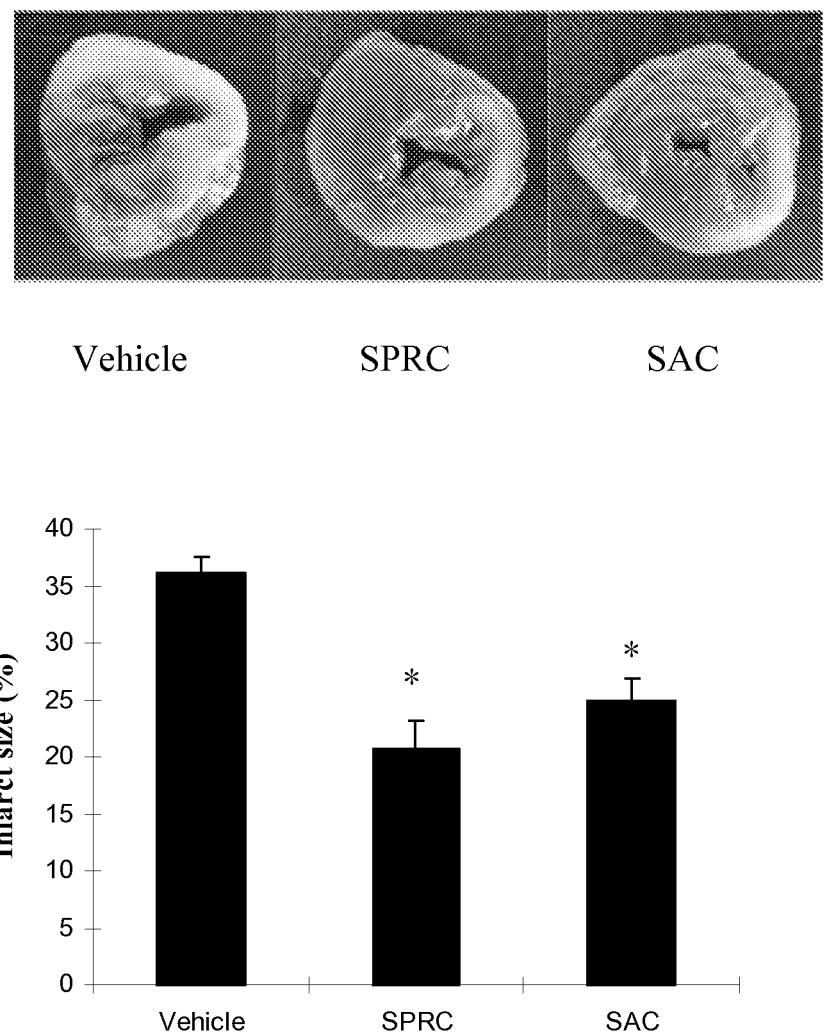
FIG. 12 shows effects of SPRC and SAC on ischemic myocardial infarction of rat heart
Figure 13:
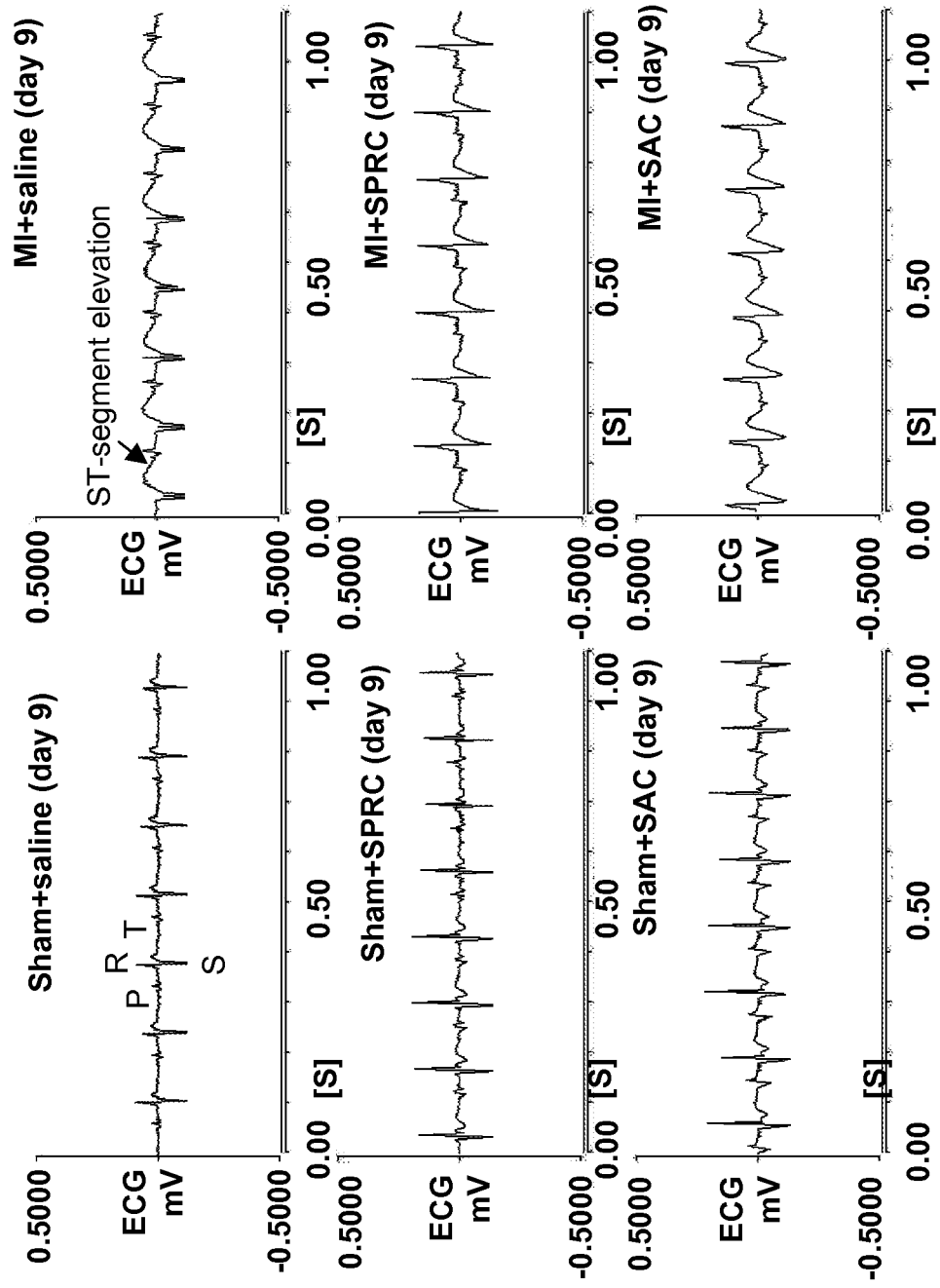
FIG. 13 shows ECG diagrams of effects of SPRC and SAC on ischemic myocardial infarction of rat heart
Figure 14A:
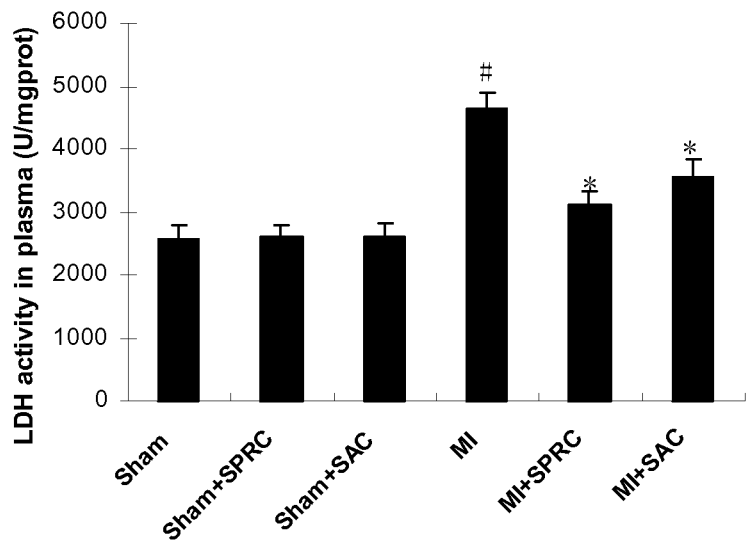
FIG. 14 shows effects of SPRC and SAC on serum LDH, CK, MDA and SOD levels of ischemic myocardial infarction of rat heart
Figure 14B:
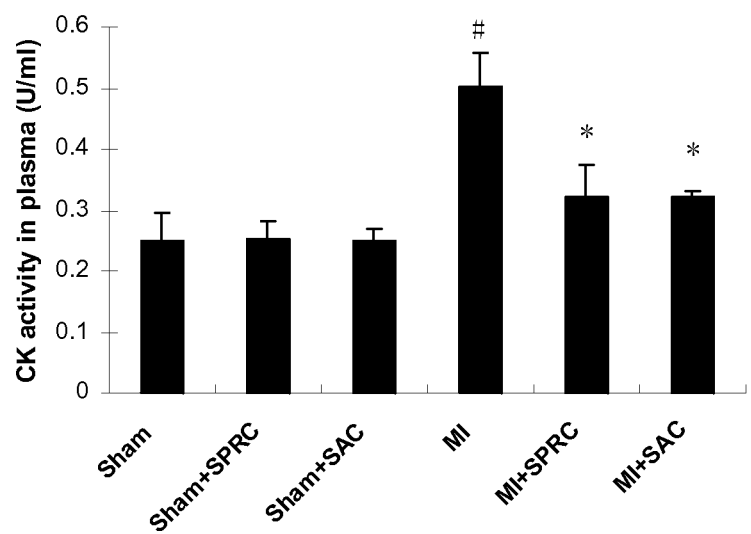
Figure 14C:
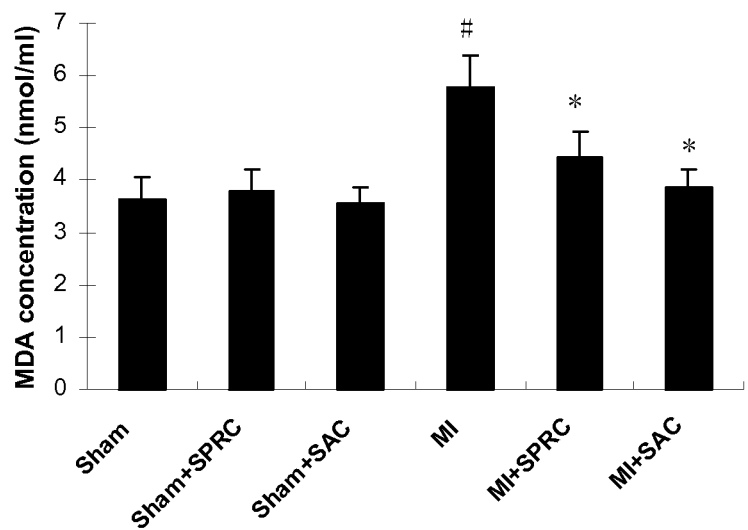
Figure 14D:
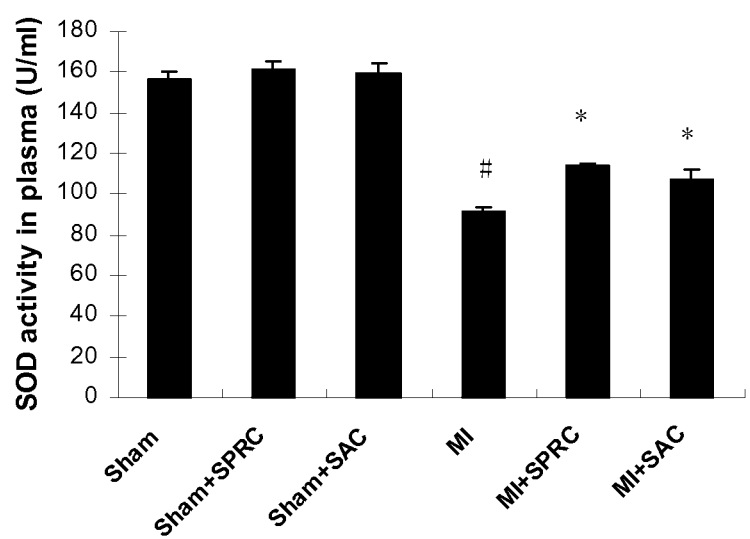

To evaluate the effect of SPRC and SAC on MI, infarct size of heart tissue are measured after TTC staining (FIG. 12). The infarct size/total area of left ventricle was significantly less in rats subjected to SPRC and SAC treatments than in vehicle injected rats. ECG patterns were similar in all groups prior to the start of the treatment as well as one week after treatment (FIG. 13).

Serum CK levels and LDH leakages are decreased after SPRC and SAC treatment of the animals. Lipid peroxidation reduced since SPRC and SAC inhibit creation of oxygen free radicals therefore inhibit lipid peroxidation, so that the product of lipid peroxidation MDA content decreased. SOD (superoxide dismutase) activity is elevated in SPRC and SAC treated animals (FIG. 14).

Figure 15A:
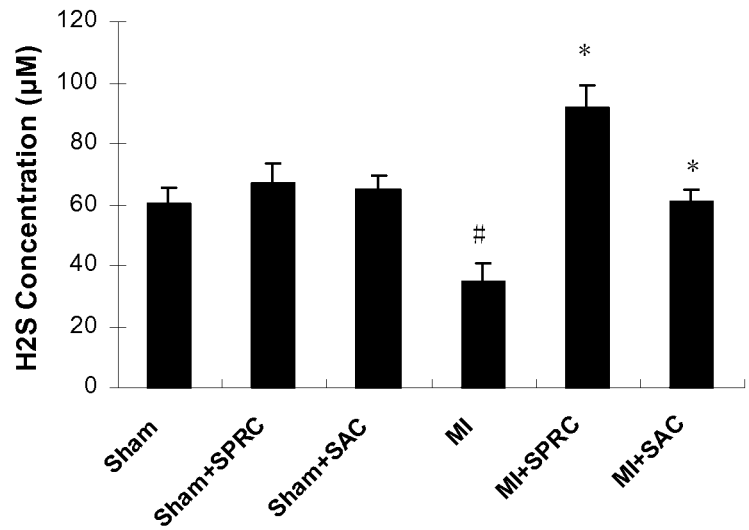
FIG. 15 shows effects of SPRC and SAC on serum $H_2S$ level and CSE activity of ischemic myocardial infarction of rat heart

Plasma levels of $H_2S$ in animal groups treated with SPRC or SAC are increased. CSE activity in animal groups treated with SPRC or SAC are increased, indicating that CSE mediates the endogenous production of $H_2S$ in mammals (FIG. 15A, B).

Figure 16:
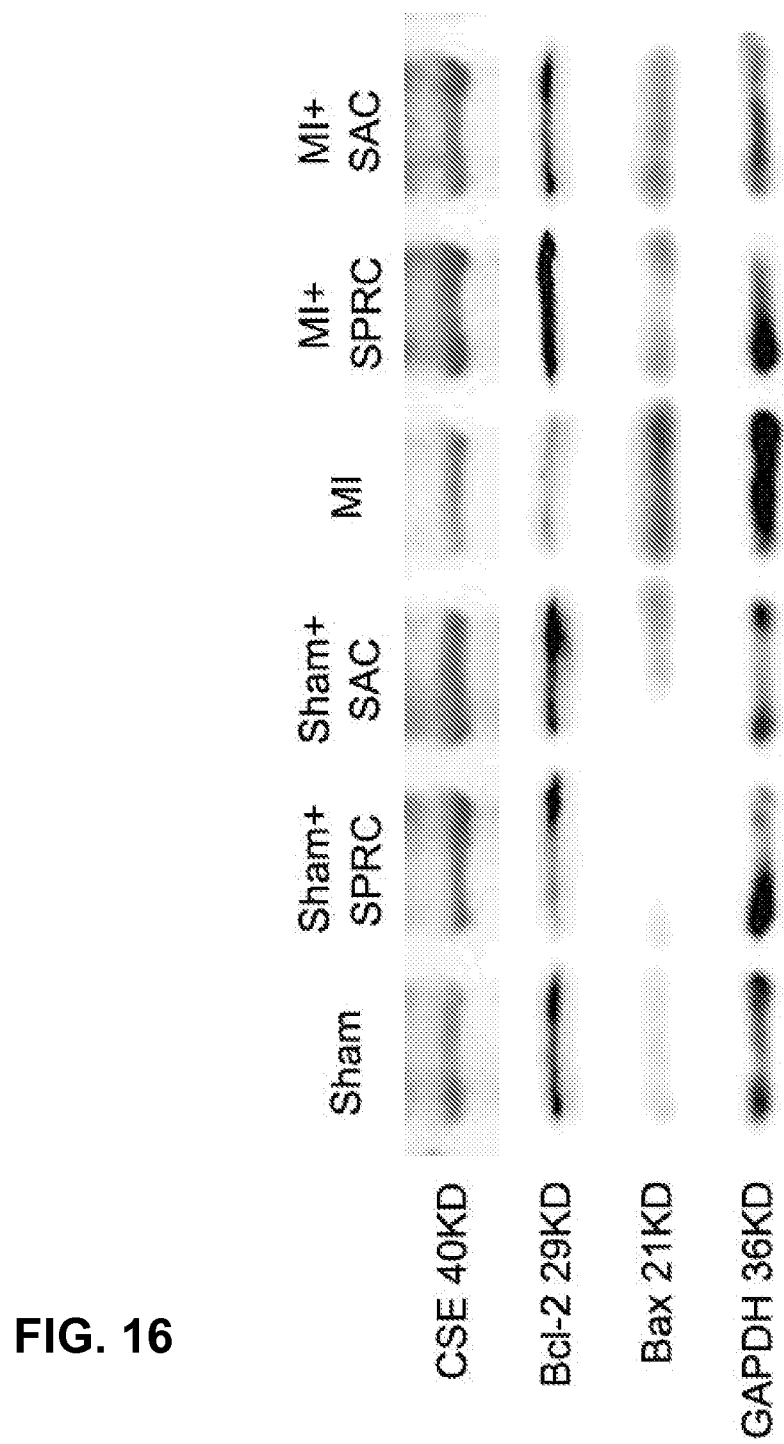
FIG. 16 shows effects of SPRC and SAC on protein expressions of Bcl-2, Bax and CSE in left ventricle of ischemic myocardial infarction of rat heart

Bax expression, which is related to cell injuries and apoptosis, is down regulated in animal groups treated with SPRC or SAC. Bcl-2 expression, which is anti-apoptotic, and CSE protein expression, which CSE mediates the endogenous production of $H_2S$ in mammals, are up regulated (FIG. 16).

Figure 17:
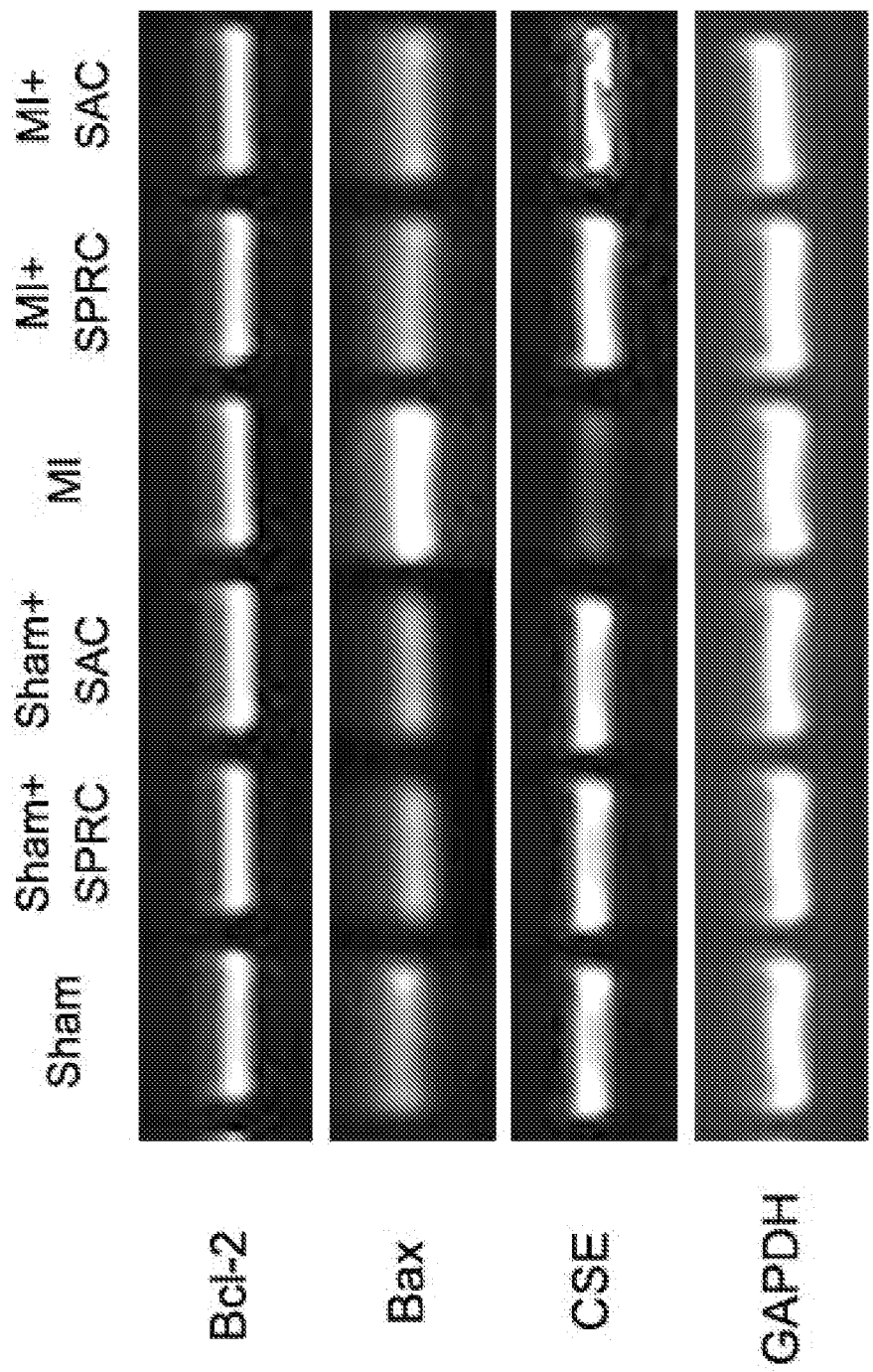
FIG. 17 shows effects of SPRC and SAC on gene expressions of Bcl-2, Bax and CSE in left ventricle of ischemic myocardial infarction of rat heart

The expressions of Bcl-2, Bax and CSE mRNAs confirm that the effects of SPRC and SAC on the animals. Similarly, Bax gene expression is down regulated, and CSE gene is up regulated in SPRC and SAC treated group. SPRC and SAC have no effects on gene expression of Bcl-2. (FIG. 17).

In summary, SAC analogues are effective to treat myocardial infarction by inducing a number of biochemical changes, which is manifested in biochemical marker changes. The mechanism of SAC analogues increases the number of surviving myocardial cells under ischemic condition is mediated by inducing biochemical changes in the cells via modulation of endogenous $H_2S$ level.

EXAMPLES

Example 1

Sac and Analogue's Effect on Improving Survival Rate of Myocardial Cells after Myocardial Infarction is Mediated Via Modulation of Endogenous $H_2S$ The heart sample of 3 day old Sprague-Dawley (SD) rat (first generation) was washed in PBS (phosphate balanced solution) under sterilized condition. The sample is digested in 0.08% trypsin solution 37 degree C. for 10 minutes in a flask, wherein the solution was stirred constantly. In order to stop the digestion, serum was added into the flask and mixed with the solution. The digesting process was repeated 8 times, and the supernatant of each digestion was collected. The supernatant was centrifuged 2,000×g for 5 minutes, and the myocardial cells were collected each time. The myocardial cell density was adjusted to $10^6$/sample and cultured in DMEM containing 10% fetal bovine serum for 3 days.

The cultured myocardial cells were divided into the following groups:

Control group, no SAC analogues treatment, no hypoxia/reoxygenation process.

Hypoxia/reoxygenation (Vehicle) group, no SAC analogues treatment, under hypoxia condition for 6 hours then cultured under condition of reoxygenation.

SAC and analogue groups, under hypoxia condition for 6 hours then cultured under condition of reoxygenation with corresponding treatment of SAC and analogues $10^{-5}$ mol/L.

Myocardial cell viability was assessed by MTT method, which is the measurement of the reduction of 3-(4,5-dimethylthiazol-2-yl)-2,5-diphenyltetrazolium bromide (MTT). MTT (0.5 mg/ml) was added to 100 μl of cell suspension (5×10³ cells/well in 96-well plates), cultured for 4 hr and a dark blue formazan (dye) product was produced in the culture. The amount of formazan was measured using a microplate reader at spectrum 570 nm.

The result (FIG. 1) shows that myocardial cell survival rate in Vehicle group was 54.35% lower than that of Control group. SAC and analogues can significantly increase the survival rate of myocardial cell under hypoxia/reoxygenation condition. All values are presented as means and standard deviations. One-way analysis of variance (ANOVA) was used to examine differences between the control group and the trial group at each time point. The LSD procedure was used for pairwise comparisons. Alpha set at 0.05, and all tests were two-tailed. All analyses were performed using SPSS 12.0.

Endogenous $H_2S$ was assessed by the following method:

The supernatant from each group of the previous cultured myocardial cell experiments was measured, and 500 μl of the supernatants from each group was taken into a test tube. Then each test tube was added 250 μl zinc acetate, 133 μl N,N-dimethyl-pphenylenediamine sulphate (20 mM), 133 μl $FeCl_3$ (20 mM), shaken well. Each of the mixture in the test tube was allowed to react in room temperature for 10 minutes, then was added 10% Trichloroacetic acid to precipitate protein. The test tubes were centrifuged 10,000×g for 10 minutes, and the photo absorption of each test tubes was measured on a spectrophotometer at 670 nm.

Figure 2:
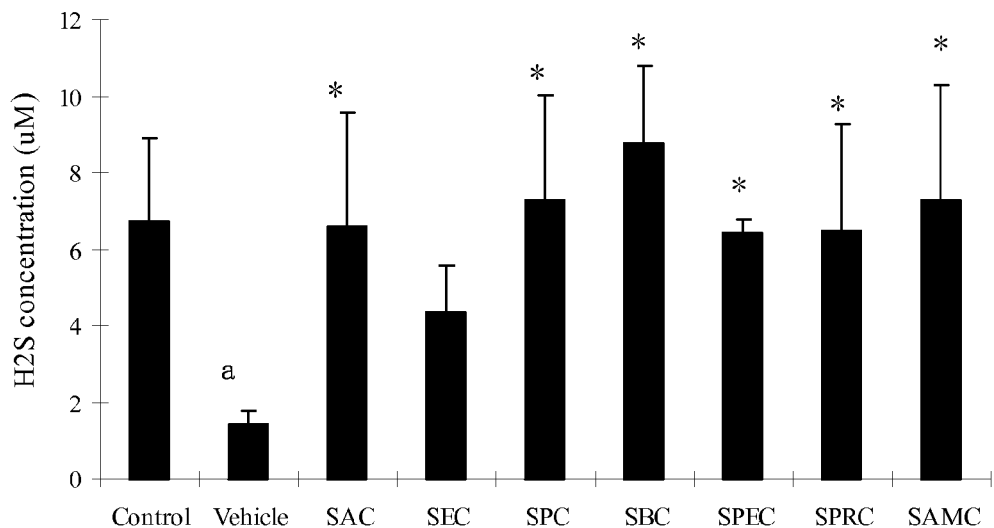
FIG. 2 shows effects of SAC and analogues on $H_2S$ concentration of myocardial cells under hypoxia/reoxygenation condition

The result (FIG. 2) shows that endogenous $H_2S$ in Vehicle group was lower than that of Control group except that of the SEC group, the differences are p<0.05 statistically significant by One-way analysis of variance analysis. SAC and analogues can significantly increase the endogenous $H_2S$ from myocardial cell under hypoxia/reoxygenation condition, since the $H_2S$ levels in the supernatants from these groups (except that of the SEC group) differed from the Vehicle group. All values are presented as means and standard deviations. One-way analysis of variance (ANOVA) was used to examine differences between the Control group and the trial group at each time point. The LSD procedure was used for pairwise comparisons. Alpha set at 0.05, and all tests were two-tailed. All analyses were performed using SPSS 12.0. (The symbol * indicates the difference is significant, and # indicates the difference between PAG negative and PAG inhibition experiments is significant. The symbol $^a$ indicates the difference between Control group and Vehicle group)

Example 2

Sac and Analogue's Effect on Lowering LDH Leakage from Hypoxia/Reoxygenation Injured Myocardial Cells Myocardial cell samples were obtained from the same procedure of Example 1, the experiment groups were divided and hypoxia/reoxygenation experiments were performed on Control group (sample n=4), Vehicle group (sample n=4), SAC and analogue groups (each group sample n=4) same as the experiments in Example 1 with the same dosages and same conditions. Myocardial cells were obtained from each sample ($10^6$ myocardial cells/sample) from the Control group, Vehicle group, SAC and analogue groups. The cells were lysed under sterilized condition, and LDH (Lactate Dehydrogenase) contents in each sample of the cells were tested by pyruvic acid production method, using LDH content in Control sample cells as standard of 100%. The rate of LDH leakage was calculated, which is the difference between LDH content of Control group samples and LDH content of Vehicle group or SAC and analogue groups. LDH leaking rate=(LDH content of Control group samples−LDH content of Vehicle group (or SAC and analogue groups))/LDH content of Control group samples×100%. Each of the SAC and analogue groups was further applied PAG (propargylglycine) in the experiments to block $H_2S$ production by the injured myocardial cells.

Figure 3:
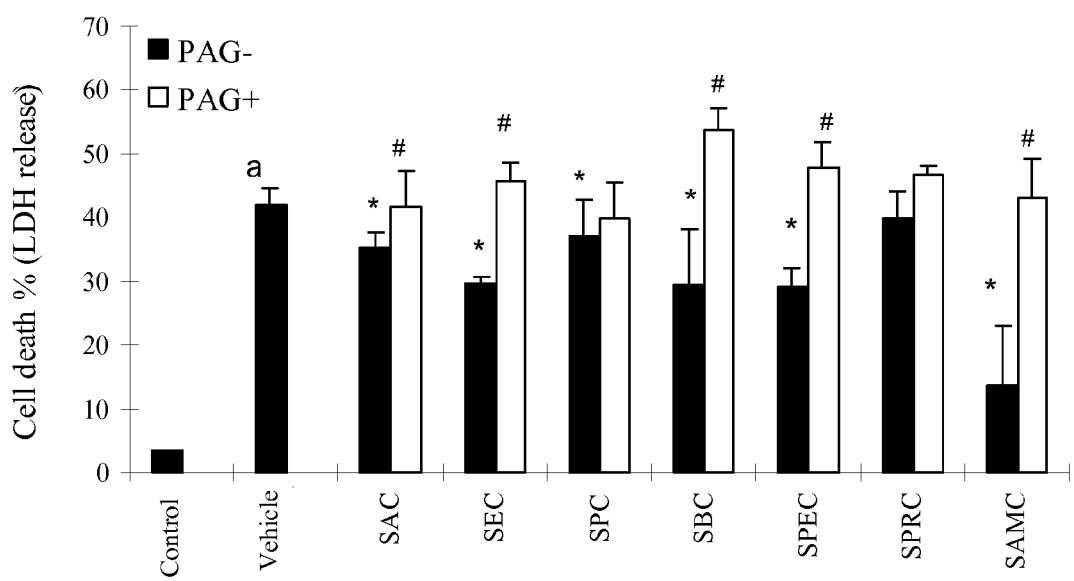
FIG. 3 shows effects of SAC and analogues on cell death rate of myocardial cells under hypoxia/reoxygenation condition

The result (FIG. 3) showed that LDH leakage rates in SAC and analogue groups were lower than that of Vehicle group except that of SPRC group, the difference were p<0.05 statistically significant by One-way analysis of variance (ANOVA) analysis. Therefore SAC and analogues can significantly lower LDH leaking rates from myocardial cell under hypoxia/reoxygenation process.

PAG blocked endogenous $H_2S$ in myocardial cells in SAC and analogue groups (FIG. 3) except that of SPRC group, the differences were p<0.05 statistically significant by one-way analysis of variance analysis. The result indicated that the reduction of LDH leakage rates in SAC and analogue treated cells are correlated with the survival rate of myocardial cell under hypoxia/reoxygenation process, which is mediated by endogenous $H_2S$ in the injured myocardial cells. (The symbol * indicates the difference is significant, significant. The symbol $^a$ indicates the difference between Control group and Vehicle group.)

Example 3

Sac and Analogue's Effects on Elevating the Activities of Sod, Catalase and Inhibiting the Creation of Free Radicals in Hypoxia/Reoxygenation Injured Myocardial Cells Myocardial cell samples were obtained from the same procedure of Example 1, the experiment groups were divided and hypoxia/reoxygenation experiments were performed on Control group, Vehicle group, SAC and analogue groups, same as the experiments in Example 1 with the same dosages and same conditions. Myocardial cells were obtained from each sample ($10^6$ myocardial cells/sample) from the Control group, Vehicle group, SAC and analogue groups. The cells were lysed under sterilized condition, and SOD (superoxide dismutase) activities in each sample of the cells were determined by Hydroxylamine method (a conventional method well known in the arts) using each microgram of protein per 1 milliliter reaction solution inhibits SOD activity to its 50% of original activity, in which the amount of SOD used in the reaction as standard of 1 unit of SOD activity.

Figure 4:
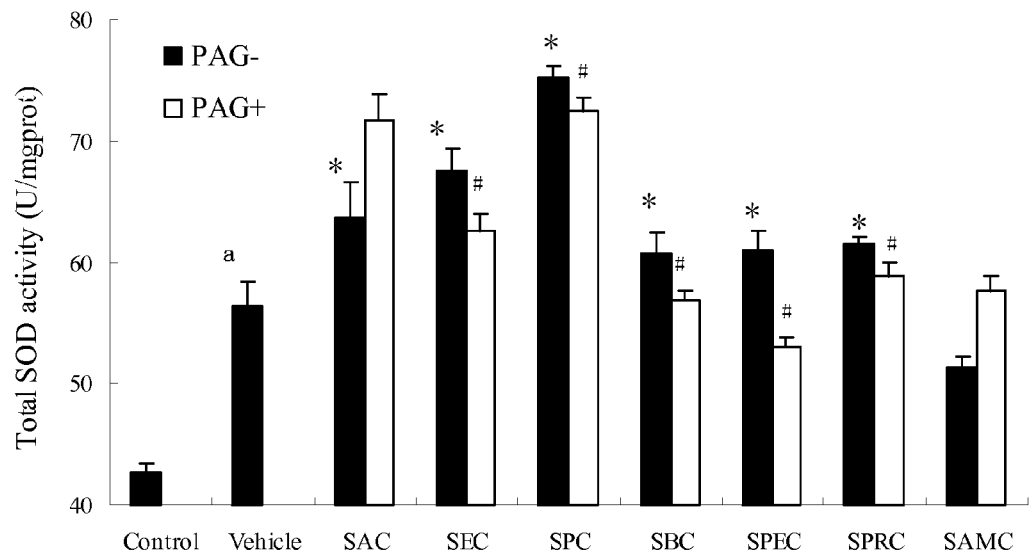
FIG. 4 shows effects of SAC and analogues on SOD activity of myocardial cells under hypoxia/reoxygenation condition

The result (FIG. 4) showed that SOD activity in SAC and analogue groups were elevated than that of Vehicle group except that of SAMC group, the difference were $p<0.05$ statistically significant by one-way analysis of variance analysis. Therefore SAC and analogues can significantly increase the SOD activity in myocardial cell under hypoxia/reoxygenation condition.

PAG reversed SAC and analogue's effect on elevating SOD activity in SAC and analogue groups (FIG. 4), the difference were $p<0.05$ statistically significant by one-way analysis of variance analysis. (The symbol * indicates the difference is significant, and # indicates the difference between PAG negative and PAG inhibition experiments is significant. The symbol $^a$ indicates the difference between Control group and Vehicle group)

Figure 5:
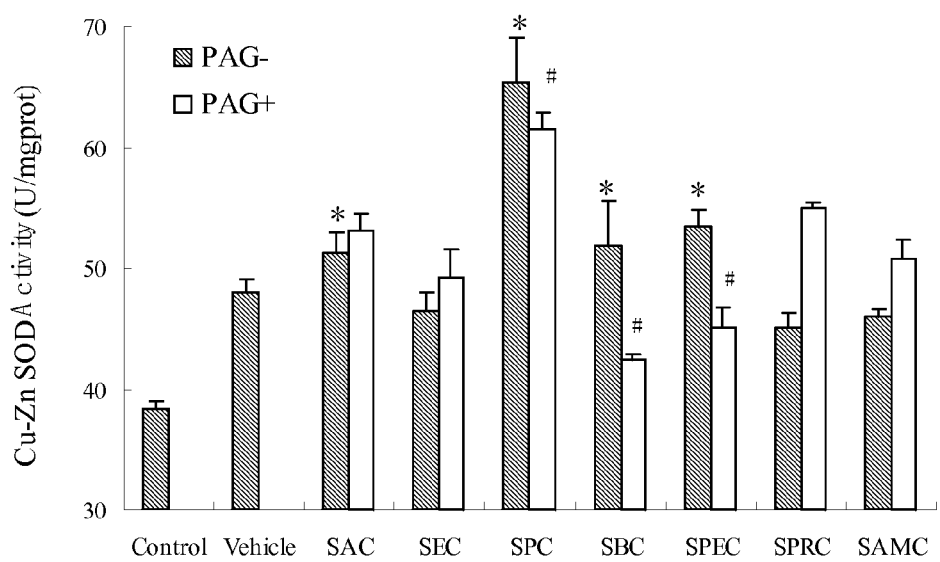
FIG. 5 shows effects of SAC and analogues on Cu—Zn SOD activity of myocardial cells under hypoxia/reoxygenation condition

SOD subtype tests further revealed that the analogues SPC, SBC and SPEC which have saturated carbon chain in their molecular structures are able to elevate the activities of Cu—Zn SOD in cytoplasm in myocardial cell under hypoxia/reoxygenation condition (FIG. 5). PAG also reversed the effect on elevating SOD activity of SPC, SBC and SPEC.

Figure 6:
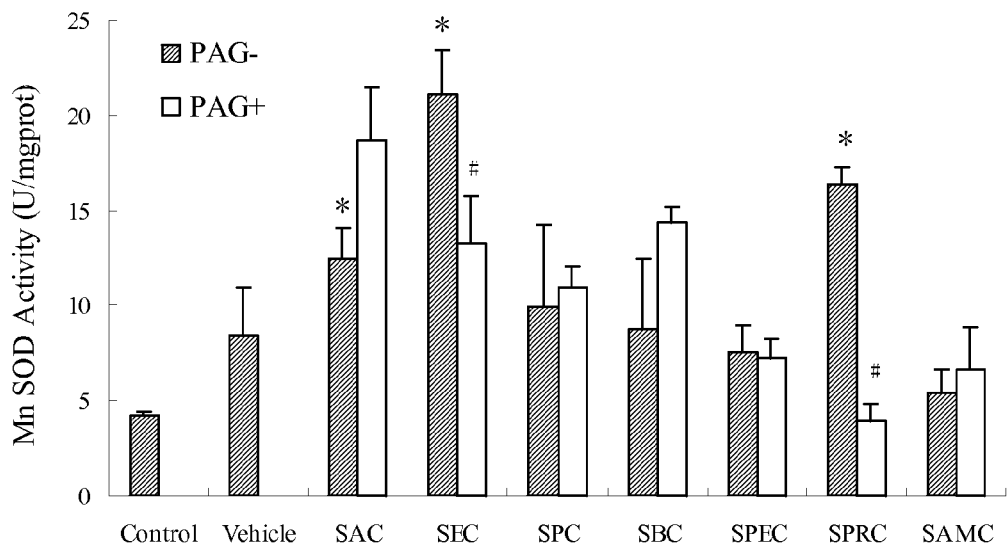
FIG. 6 shows effects of SAC and analogues on Mn SOD activity of myocardial cells under hypoxia/reoxygenation condition

SPRC and SEC were able to elevate Mn-SOD activity in mitochondria in myocardial cell under hypoxia/reoxygenation condition (FIG. 6). PAG also reversed the SAC and analogue's effects on elevating SOD activity of SPRC and SEC, indicating that SAC and analogues are able to increase the activity of SOD significantly in myocardial cell under hypoxia/reoxygenation condition, which may be correlated with endogenous $H_2S$ in the injured myocardial cells.

The activities of Catalase in each sample of the cells from the Control group, Vehicle group, SAC analogue groups were determined by Catalase-hydrogen peroxide method during which Catalase was used to catalyze excessive hydrogen peroxide ($H_2O_2$). The resulted red colored product N-(4-antipyryl)-3-chloro-5-sulfonate-p-benzpquinonemonoimine was assessed at a spectrophotometer at 520 nm.

Figure 7:
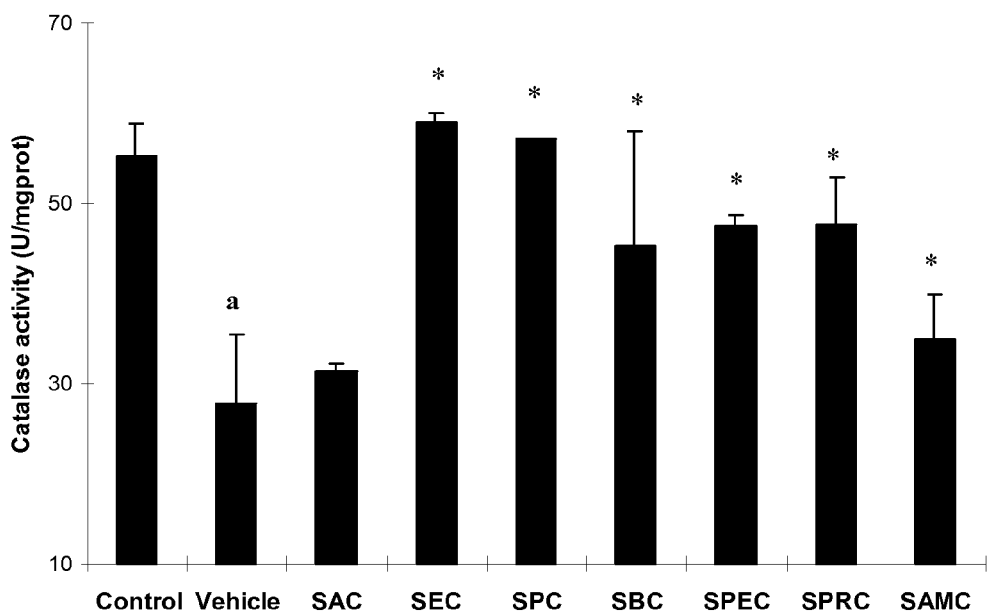
FIG. 7 shows effects of SAC and analogues on Catalase activity of myocardial cells under hypoxia/reoxygenation condition

One enzyme activity unit (U) is the amount of Catalase catalyzes 1 μmole $H_2O_2$ at 25 degree C., pH 7.0 in 1 minute. The results (FIG. 7) showed that the Catalase activity in hypoxic cells of Vehicle group was significantly lower than that of control group ($p<0.05$), while the Catalase activity in SAC analogue treated ischemic cells groups were all elevated ($p<0.05$).

Figure 8:
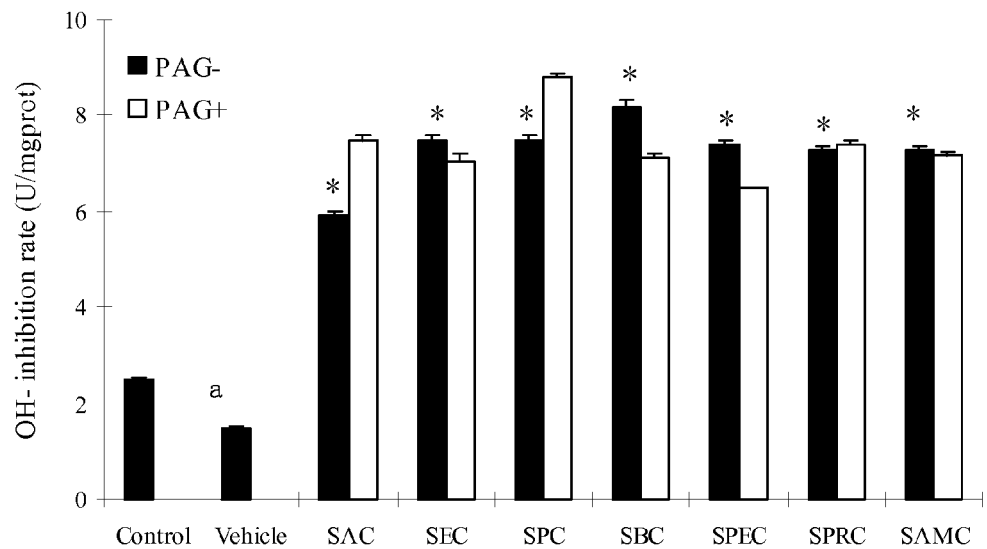
FIG. 8 shows effects of SAC and analogues on OH⁻ inhibition rate of myocardial cells under hypoxia/reoxygenation condition

In Fenton reaction, which is a major reaction producing $OH^-$ in an organism's body, the amount of $OH^-$ is proportional to the amount of $H_2O_2$ produced by Fenton reaction. The product can be given electron receptor, and reacted with gress chromogenic reaction to produce red colored material, which can be detected at a spectrophotometer at 550 nm. The results (FIG. 8) showed that the $OH^-$ inhibition rates in hypoxic cells treated with SAC analogues were significantly higher than that of Control group ($p<0.05$), indicating that SAC analogues can significantly inhibiting $OH^-$ production in hypoxic myocardial cells. The inhibition effect could not be reversed by PAG.

Example 4

Figure 9:
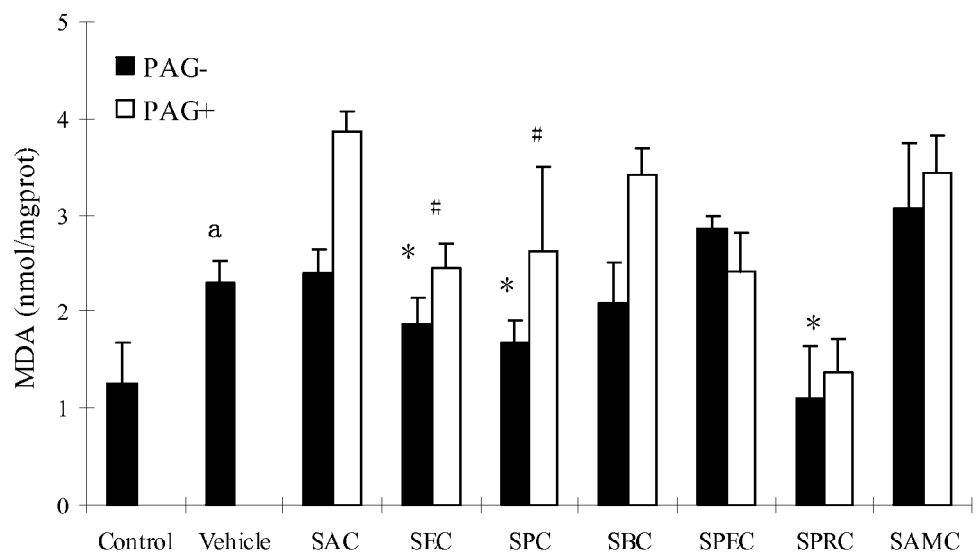
FIG. 9 shows effects of SAC and analogues on MDA content of myocardial cells under hypoxia/reoxygenation condition
Figure 10:
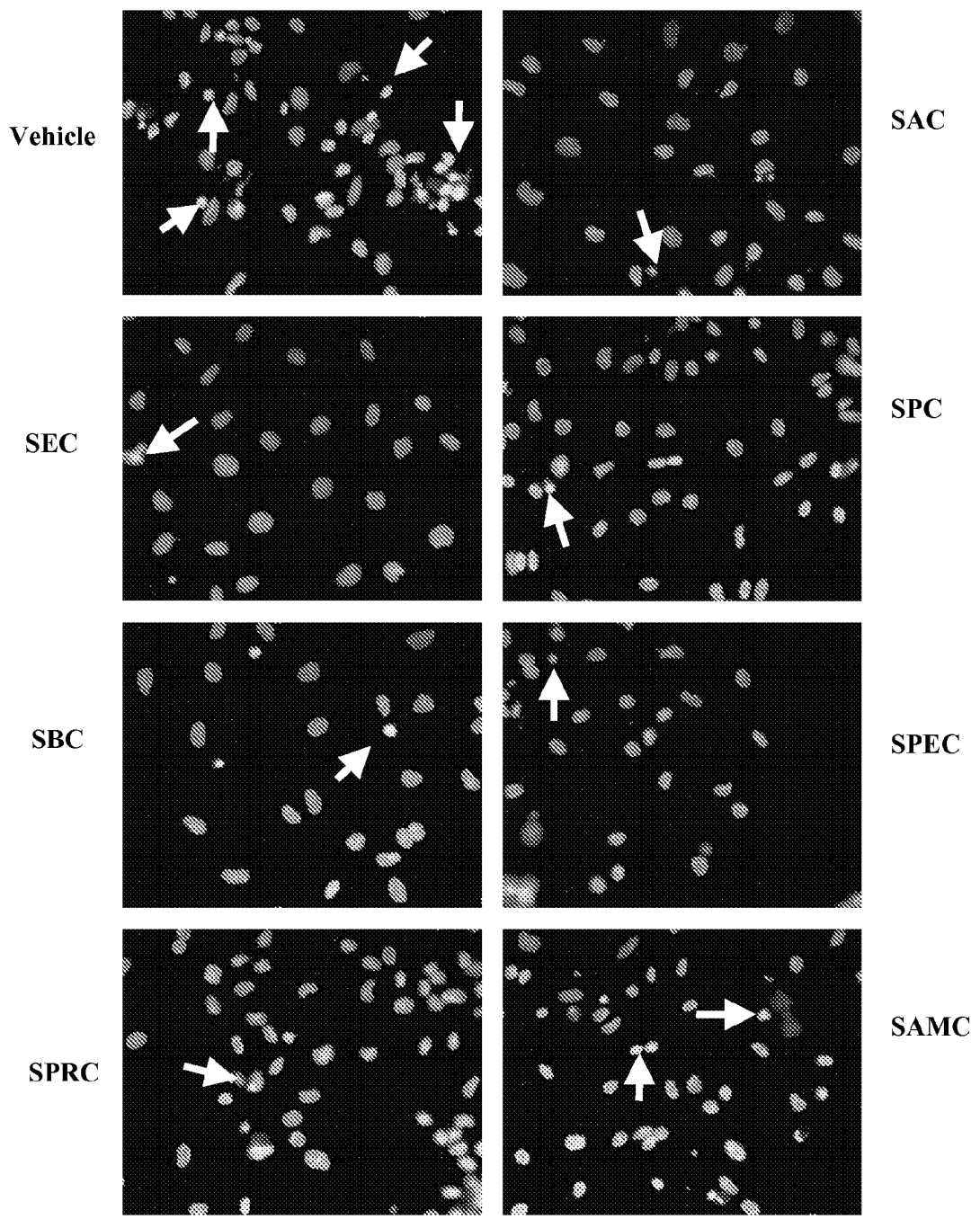
FIG. 10 shows effects of SAC and analogues on cell apoptosis of myocardial cells under hypoxia/reoxygenation condition, the arrows pointing to apoptotic cell nuclei stained dark

Sac and Analogue's Effect on Inhibiting Lipid Peroxidation in Hypoxia/Reoxygenation Injured Myocardial Cells Myocardial cell samples were obtained from the same procedure of Example 1, the experiment groups were divided and hypoxia/reoxygenation experiments were performed on Control group, Vehicle group, SAC and analogue groups, same as the experiments in Example 1 with the same dosages and same conditions. Myocardial cells were obtained from each sample ($10^6$ myocardial cells/sample) from the Control group, Vehicle group, SAC and analogue groups. The cells were lysed under sterilized condition, and lipid peroxidation experiments on the samples were performed. Since oxygen free radical attacks poly unsaturated fatty acid in biomembrane, inducing lipid peroxidation and producing MDA (malondialdehyde). MDA can react with thiobarbituric acid (TBA), forms red product, which can be detected in spectrophotometer at 532 nm. The results (FIG. 9) showed that the lipid peroxidation in hypoxic cells in Vehicle group was significantly higher than that of Control group ($p<0.05$), and the lipid peroxidations in hypoxic cells treated with SAC analogues SEC, SPC, SPRC were inhibited by SAC analogues. The results indicated that SAC analogues can significantly inhibiting lipid peroxidation in hypoxic myocardial cells. The inhibition effect could be reversed by PAG.

Example 5

Sac and Analogue's Effect on Inhibiting Apoptosis of Hypoxia/Reoxygenation Injured Myocardial Cells Myocardial cell samples were obtained from the same procedure of Example 1, the experiment groups were divided and hypoxia/reoxygenation experiments were performed on Control group, Vehicle group, SAC and analogue groups, same as the experiments in Example 1 with the same dosages and same conditions. Myocardial cells from the Control group, Vehicle group, SAC and analogue groups were stained with Hoechst stain (a nuclear staining for assessment of apoptosis). The morphology of nuclear chromatin was assessed by staining with the fluorescent dye Hoechst 33342. Cells were washed in PBS and then stained with Hoechst 33342 (10 μg/ml) at 37 degree C. Cells were washed again with PBS and fixed with 3.7% paraformaldehyde (v/v). Each field of cells was photographed twice (magnification, ×400), using appropriate filters to examine and compare Hoechst 33342 and staining in the cells.

Myocardial cell apoptosis is of great damage to cardiac structure and function, and is one of the major reason for cardiac failure. The results indicate that SAC analogues can inhibit myocardial cell apoptosis, and have great value in application of treating heart disease.

Example 6

Synthesis of S-propargyl-cysteine (SPRC)

Figure 11:
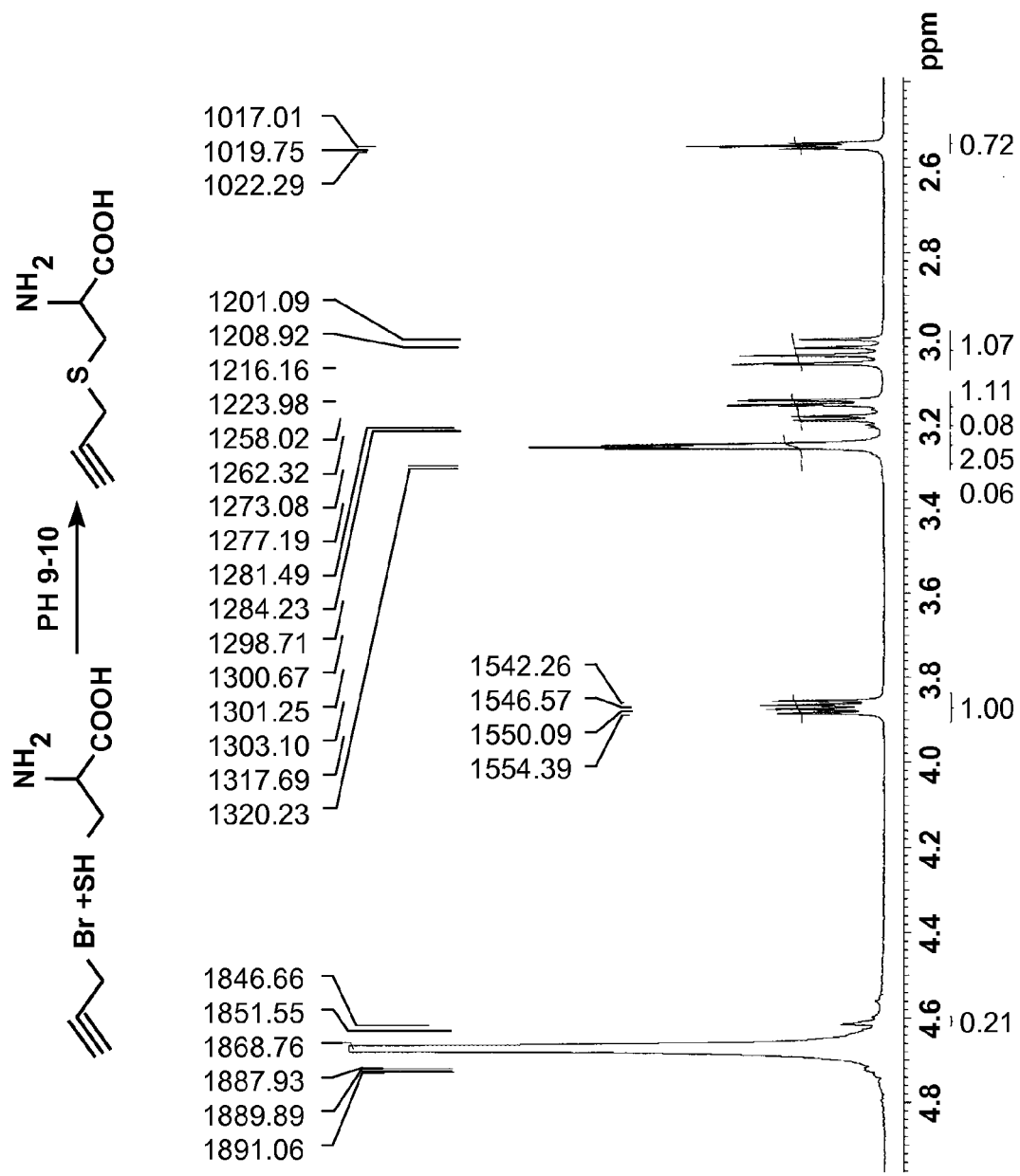
FIG. 11 shows the chemical structure of synthesized SPRC determined by Proton Nuclear Magnetic Resonance Spectroscopy

SPRC is synthesized from L-cysteine hydrochloride and 3-bromopropene with the following steps. L-cysteine hydrochloride in $NH_4OH$ (2M, 240 ml) is prepared and pre-cooled to 0 degree C. Then propargyl bromide (14.5 g, 0.124 mol) is added to the ice-cooled solution of L-cysteine hydrochloride in $NH_4OH$. The mixture is stirred vigorously at 0 degree C. for 2 h and filtered, and the filtrate was concentrated in vacuum at the temperature less than 40 degree C. to a small volume, and filtered again. The solid is washed repeatedly with ethanol, dried in vacuum, and re-crystallized from 2:3 $H_2O/C_2H_5OH$ to yield purified SPRC in white needle crystal appearance. The chemical structure of SPRC is determined by Proton Nuclear Magnetic Resonance Spectroscopy (FIG. 11).

Example 7

Effects of SPRC and SAC on Infarct Size in Rats Following MI Injury

SPRC and SAC were dissolved in saline (vehicle). Male SD rats (weight 200-250 g) were randomly assigned to four treatment groups: group (1) Sham group: Sham-treated with saline (n=4), (2) Sham+SPRC group: Sham-treated with SPRC (50 mg/Kg/day) (n=4), (3) Sham+SAC group: Sham-treated with SAC (50 mg/Kg/day) (n=4), (4) MI group: MI treated with saline (n=8), (5) MI+SPRC group: MI treated with SPRC (50 mg/Kg/day) (n=8), (6) MI+SAC group: MI treated with SAC (50 mg/Kg/day) (n=8). Rats were pre-treated for seven days with each SAC analogues respectively via an intraperitoneal injection once daily before they were used for MI model studies.

MI was induced on day eight by ligation of the left anterior descending coronary artery at T approximately 2-3 mm from its origin. Briefly, the rats were anesthetized with 7% choral hydrate (60 mg/kg intraperitoneal injection), endotracheally intubated and mechanically ventilated with room air, respiratory rate 100 breaths/min, tidal volume 2.5 ml with a rodent ventilator (DHX-150, China). ECG was recorded in the anaesthetized animal for a period of one minute using the Animal Mflab200 amplifier (Produced in China). A left thoracotomy was performed and the third intercostal space was exposed. The proximal left anterior descending coronary artery, which supplies blood to left ventricle, was ligated at the position 2-3 mm from the aorta with a 5-0 atraumatic suture that was passed through the superficial layers of myocardium, between the left auricle and the cone of pulmonary artery. The MI model was considered completely established when the area of myocardium supplied by the ligated coronary artery turned to pallor, and ECG recording showed the ST segment was elevated. Then incisions were sutured and the chests were closed. Sham operated rats were prepared in the same manner except the left coronary was not ligated. After completion of the surgical procedures, rats were removed from the ventilator and the endotracheal tube removed. The rats were kept warm, given water and food after they were awake from the anesthesia and kept in different cages according to experiment groups. The rats in correspondent experiment groups were given SPRC or SAC continuously for 2 more days, while the rats in control and MI groups were given no SAC analogues.

Forty eight hours after the surgery, ECG was recorded for each rat in each group. Blood samples were taken from abdominal aorta from each rat in each group. Then the rats were sacrificed and their hearts were taken, put into TTC solution, pH 7.4 at 37 degree C. for 15 minutes. The heart tissues from the rats were stained and the myocardial infarction areas are observed.

To evaluate the effect of SPRC and SAC on MI, infarct size were measured after TTC staining (FIG. 12). The infarct size/total area of myocardium was significantly less in rats subjected to SPRC and SAC treatments than in saline (vehicle) injected rats, 20.8±2.4% and 24.9±1.9% vs. 36.0±1.3% respectively ($p<0.05$). However, differences in ECG patterns were similar in all groups prior to the start of the treatment as well as one week after treatment (FIG. 13), All rats showed significant ST elevation, which is characteristic of MI. ECG charts of rats that underwent the MI procedure recorded on day 10, 48 hr after the induction of MI showed that SAC and SPRC groups had a less elevated ST-segment. In addition, Pathological Q waves which may occur in the early stage of MI were observed in the ECG charts of all treatment groups.

Example 8

Effects of SPRC and SAC on Lactate Dehydrogenase (LDH), Creatine Kinase (CK) Leakage, Malondialdehyde (MDA) Levels, and Superoxide Dismutase (SOD) Activity in Plasma Animals were assigned and prepared the same as in Example 7, and dosages of SPRC and SAC were used the same in this example as in Example 7.

Serum CK levels were detected with diagnostic kit (NJBI, China) according to the instructions. LDH were determined calorimetrically with a spectrophotometer. Lipid peroxidation was measured in terms of MDA content using the thiobarbituric acid (TBA) assay. There were significantly higher levels of CK and LDH activity in MI groups compared to the MI+SPRC groups and MI+SAC groups ($p<0.01$, respectively). With regard to lipid peroxidation, the levels of MDA in MI groups increased at 48 h after myocardial infarction. In comparison with that in the MI group, the variation of MDA levels in SAC group decreased dramatically ($p<0.01$). The SPRC treatment group also had lower level of MDA compared to MI group ($p<0.05$). (FIG. 14)

|  | LDH (U/L) | CK (U/ml) | MDA (nmol/ml) | SOD (U/ml) |
|---|---|---|---|---|
| Sham | 2573 ± 206 | 0.249 ± 0.047 | 3.63 ± 0.41 | 156.8 ± 3.4 |
| Sham + SPRC | 2612 ± 189 | 0.251 ± 0.032 | 3.79 ± 0.40 | 161.2 ± 3.8 |
| Sham + SAC | 2599 ± 212 | 0.250 ± 0.019 | 3.57 ± 0.31 | 159.8 ± 4.8 |
| MI | 4641 ± 251# | 0.502 ± 0.055# | 5.78 ± 0.61# | 91.3 ± 2.3 |
| MI + SPRC | 3096 ± 231** | 0.322 ± 0.052* | 4.43 ± 0.51 | 113.8 ± 1.5 |
| MI + SAC | 3556 ± 291* | 0.322 ± 0.010* | 3.86 ± 0.35* | 107.1 ± 5.4 |

Example 9

Effects of SPRC on Plasma $H_2S$ Levels and Left Ventricular CSE Activity in Rats Following MI Injury Animals were assigned and prepared the same as in Example 7, and dosages of SPRC and SAC were used the same in this example as in Example 7.

The plasma levels of $H_2S$ in each treatment group were determined since CSE mediates the endogenous production of $H_2S$ in mammals. Plasma $H_2S$ concentrations in MI group rats at 48 h after MI induction were 34.7±5.6 µM (n=8). In contrast, plasma $H_2S$ concentrations were significantly increased in rats treated with SPRC 91.6±7.6 µM, (p<0.001), and SAC 61.1±3.6 µM, (p<0.01) respectively (FIG. 15A). Left ventricular CSE activity was analyzed in the tissue homogenates from each treatment group (n=6). CSE activity was 1.58±0.15 µmol/g protein/hr in left the ventricular tissues in MI group and 2.19±0.32 µmol/g protein/hr in the MI+SAC treated rats.

Figure 15B:
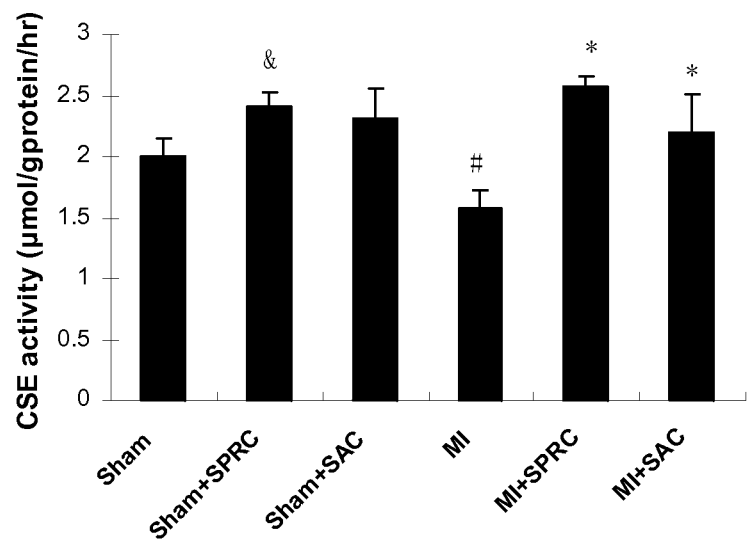

SPRC administered rats had the highest CSE activity of 2.58±0.07 µmol/g protein/hr (p<0.01) (FIG. 15B). This observation correlated with the observed increases in $H_2S$ concentrations in the same treatment groups.

|  | $H_2S$ concentration in plasma (µM) | CSE activity (µM/mgprot) |
|---|---|---|
| Sham | 60.3 ± 5.3 | 2.01 ± 0.14 |
| Sham + SPRC | 67.2 ± 6.4 | 2.41 ± 0.12 |
| Sham + SAC | 65.2 ± 4.4 | 2.31 ± 0.24 |
| MI | 34.7 ± 5.6# | 1.58 ± 0.15# |
| MI + SPRC | 91.6 ± 7.6* | 2.58 ± 0.07* |
| MI + SAC | 61.1 ± 3.6* | 2.19 ± 0.32* |

Example 10

Effects of SPRC and Sac on the Expression of Bcl-2, Bax and CSE Protein Levels in Left Ventricle Animals were assigned and prepared the same as in Example 7, and dosages of SPRC and SAC were used the same in this example as in Example 7.

Western blot analysis showed that Bax expression was highest in the MI group, Bcl-2 and CSE protein expression were decreased significantly (p<0.01 vs. Sham group). In the MI+SPRC and MI+SAC groups Bax protein levels were down-regulated (p<0.01). Moreover, Bcl-2 and CSE protein expression were up-regulated (p<0.01) (FIG. 16).

Example 11

Effects of SPRC and SAC on the expression of Bcl-2, Bax and CSE mRNA Levels in Left Ventricle Animals were assigned and prepared the same as in Example 7, and dosages of SPRC and SAC were used the same in this example as in Example 7.

To further verify the effects of SPRC and SAC, the expressions of Bcl-2, Bax and CSE mRNA were accessed by RT-PCR (FIG. 17). An isoform of the CSE gene was detected (GenBank; access no. AY641456). The relative amounts of CSE mRNA in Left ventricular subjected to MI were increase 3.3-fold and 1.5-fold following SPRC and SAC exposure as compared to the MI group. Bax gene expression was down regulated in the MI+SPRC and MI+SAC group (p<0.05). There were no significant differences of Bcl-2 gene expression in each treated groups (p>0.05).

Example 12

Effects of SPRC on Anti $H_2O_2$ Injury and Elevating the Survive Rate of H9c2 Cardiac Muscle Cells and Reducing LDH Leakage of the Cells H9c2 cells were cultured in DMEM with 10% of fetal bovine serum, 37 degree C. and 5% $CO_2$ incubator. The monolayer culture was split at a 1:4 ratio or harvested to perform experiments when confluence was 70-80%. Adjust the density of the cells to $5 \times 10^{-3}$/well and inoculate the cells on a 96 well plate.

Control group, no SAC analogues treatment, no $H_2O_2$ injured process.

$H_2O_2$ injury (Model) group, no SAC analogues treatment, under $H_2O_2$ 200 µmol/L for 2 hours.

PAG group, PAG $10^{-4}$/mol/L

SPRC dosage groups: SPRC 1E-7, SPRC 1E-6, SPRC 1E-5, the cell groups were treated with SPRC dosages of $10^{-7}$ mol/L, $10^{-6}$ mol/L, $10^{-5}$ mol/L respectively.

SPRC dosage+PAG groups: the cell group was treated with SPRC dosages of $10^{-5}$ mol/L and PAG $10^{-4}$ mol/L.

Figure 18A:
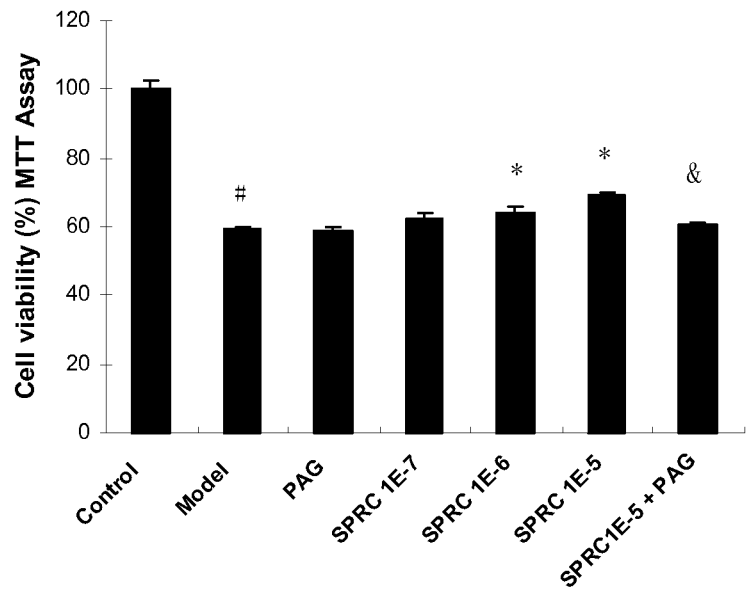
FIG. 18 shows effects of different dosages of SPRC on cell viability and cell death rates of H9c2 cells injured by $H_2O_2$.

H9c2 cell viability was assessed by MTT method. The result (FIG. 18A) showed that H9c2 cell survival rate in model group was significantly lower than that of control group. SPRC middle dose and high dose groups can significantly increase the survive rate of H9c2 cell (p<0.05). PAG is able to block the effect of SPRC.

Figure 18B:
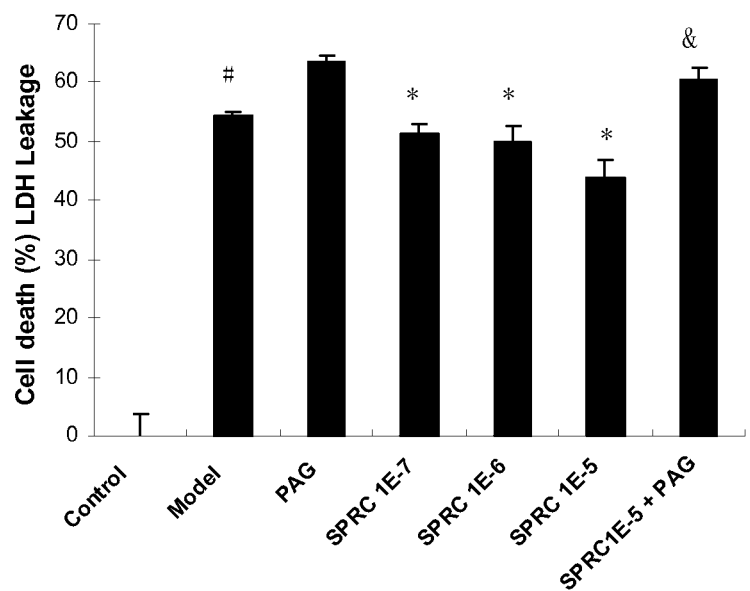

The cell samples ($10^6$ cells/sample) from each group were lysed under sterilized condition, and LDH contents in each samples were tested by pyruvic acid production method. The results (FIG. 18B) showed that SPRC groups demonstrated less LDH leakage than that of model group, and PAG could block the SPRC effect, indicating SPRC mediates its effect on H9c2 cell by way of endogenous $H_2S$.

TABLE 4

Effects of SPRC on anti $H_2O_2$ injury and elevating the survive rate of H9c2 cardiac muscle cells and reducing LDH leakage of the cells

|  | H9c2 Cell Survive (%) | LDH Leakage (%) |
|---|---|---|
| Control | 100.0 ± 2.4 | 0.0 ± 3.6 |
| Model | 59.4 ± 0.9 # | 54.2 ± 0.9 # |
| PAG Group | 58.9 ± 1.2 | 63.4 ± 1.2 |
| SPRC Low Dose | 62.4 ± 1.6 | 51.4 ± 1.8 |
| SPRC middle Dose | 64.1 ± 1.5* | 50.0 ± 2.6* |
| SPRC High Dose | 69.1 ± 1.1* | 43.9 ± 3.0* |
| SPRC + PAG | 60.9 ± 0.3& | 60.6 ± 1.9& |

Example 13

Effects of SPRC on Elevating Sod Activity and Inhibiting MDA Produced from Lipid Peroxidation in H9c2 Cardiac Muscle Cells H9c2 cells were cultured same as Example 12, the cells were then divided into the groups same as Example 12.

The cells were lysed under sterilized condition, and lipid peroxidation experiments on the samples were performed.

Figure 19A:
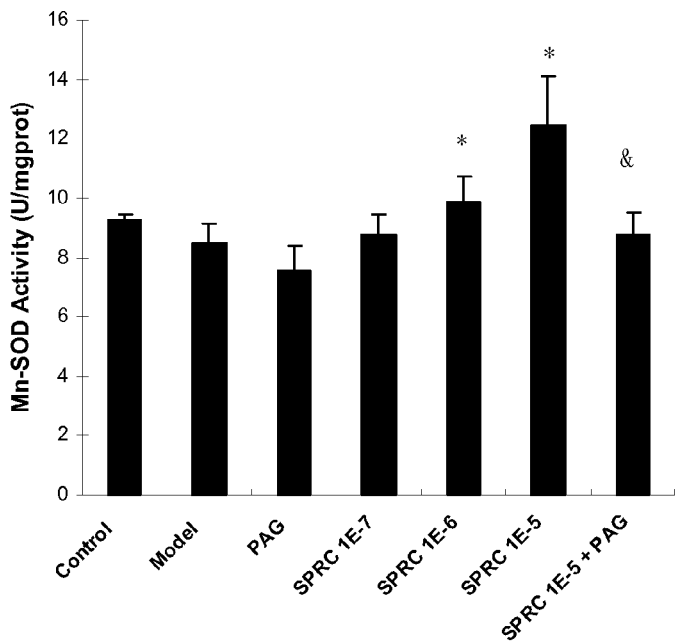
FIG. 19 shows effects of different dosages of SPRC on Mn-SOD activity and MDA level of H9c2 cells injured by $H_2O_2$.

The results (FIG. 19A) showed that SPRC middle and high dosage groups could significantly increase Mn-SOD activity (p<0.05). The effect of SPRC could be blocked by PAG, indicating SPRC mediates its effect on H9c2 cell by way of endogenous $H_2S$.

Figure 19B:
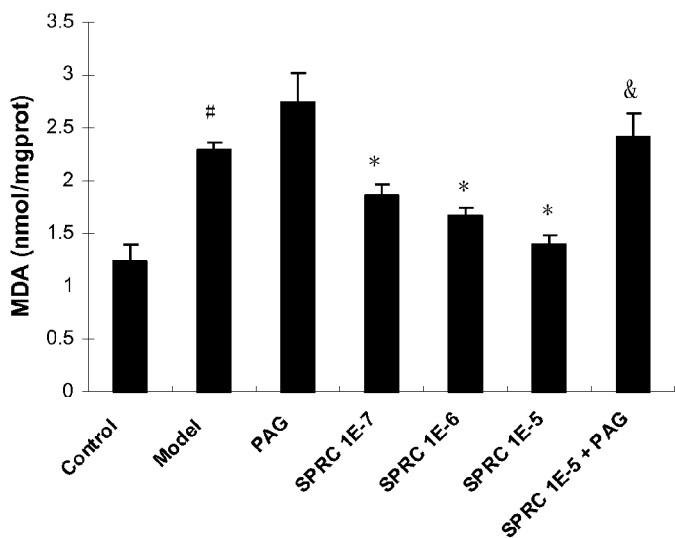
Figure 20:
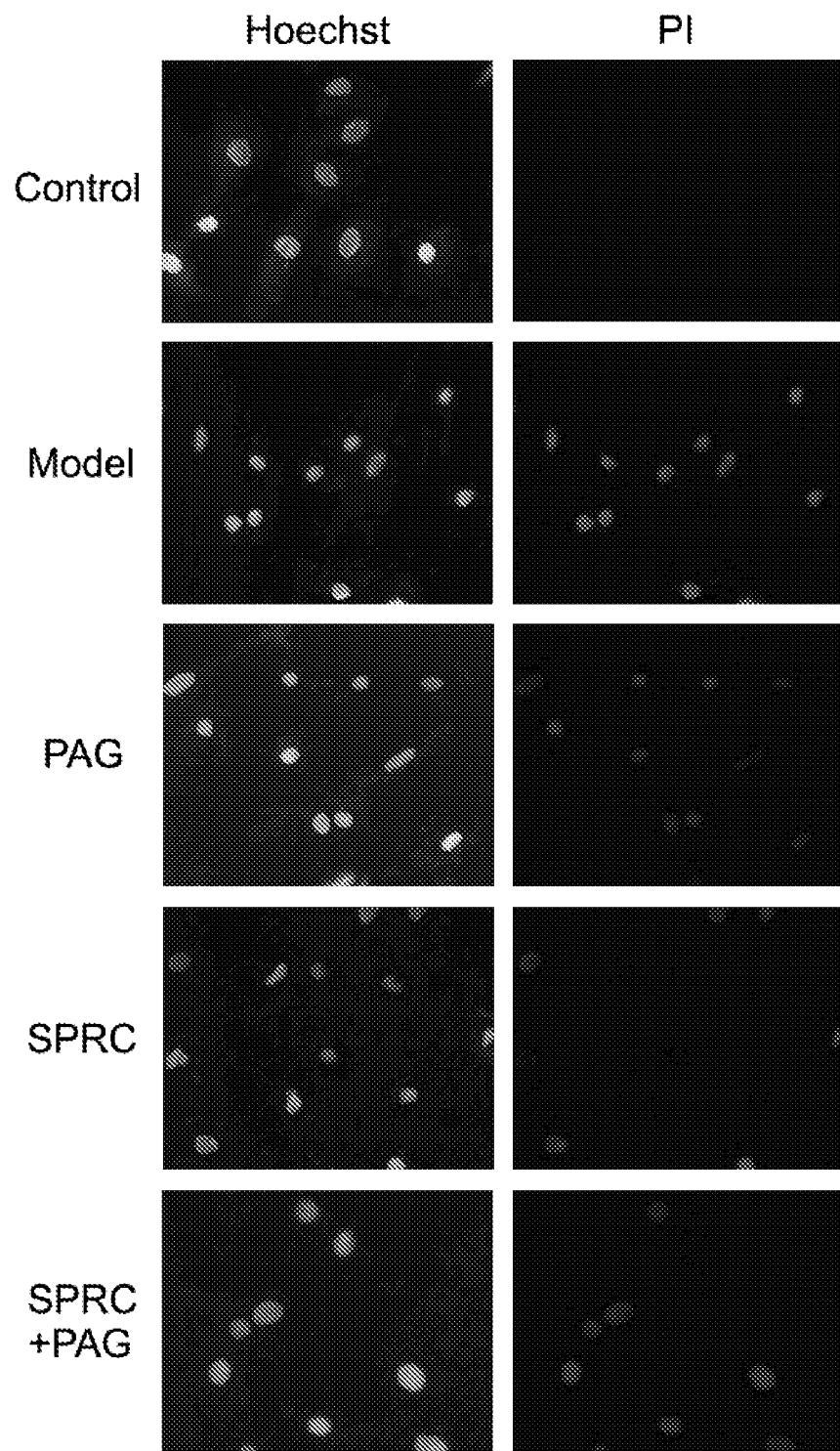
FIG. 20 shows effects of SPRC on cell apoptosis of H9c2 cells injured by $H_2O_2$.

MDA contents in model group is significantly higher than that of control group (FIG. 19B) (p<0.05). The MDA contents in SPRC low, middle and high dosage groups were lower than that of model group, and PAG could block the effect of SPRC, indicating that the effect of SPRC inhibiting lipid peroxidation is mediated by endogenous H2S.

TABLE 5

Effects of SPRC on elevating SOD activity and inhibiting MDA produced from lipid peroxidation in H9c2 cardiac muscle cells

|  | Mn-SOD Activity (U/mgprot) | MDA Content (nmol/mgprot) |
| --- | --- | --- |
| Control | 9.23 ± 0.19 | 1.25 ± 0.12 |
| Model | 8.46 ± 0.66 | 2.28 ± 0.10# |
| PAG | 7.57 ± 0.83 | 2.71 ± 0.26 |
| SPRC Low Dose | 8.75 ± 0.68 | 1.89 ± 0.09* |
| SPRC Middle Dose | 9.89 ± 0.83* | 1.70 ± 0.08* |
| SPRC High Dose | 12.45 ± 1.63* | 1.42 ± 0.04* |
| SPRC + PAG | 8.78 ± 0.74& | 2.21 ± 0.19& |

Example 14

Effects of SPRC on Inhibiting Apoptosis of H9c2 Cardiac Muscle Cells

H9c2 cells were cultured same as Example 12, the cells were then divided into the groups same as Example 12.

Hoechst and PI (propidium iodide) double stain of the samples confirmed that SPRC is effective on inhibiting apoptosis of H9c2 cells. Cells were washed in PBS and then stained with Hoechst 33342 (10 μg/ml) and propidium iodide (10 μg/ml) for 10 min at 37° C. Cells were washed again with PBS and fixed with 3.7% paraformaldehyde (v/v). Each field of cells was photographed twice (magnification, ×400), using appropriate filters to examine and compare Hoechst 33342 and PI fluorescence staining in the same cells. [/color]. Apoptosis is of great damage to the structure and the function of the heart, which leads to heart failure. This experiment provides evidences from animal model test to cell model test at genetic to protein to cell levels to prove that SPRC is able to antagonize cell apoptosis, that SPRC is valuable to treat heart disease.

Example 15

Synthesis of S-Allyl-Cysteine (SAC)

SAC is synthesized from L-cysteine hydrochloride and 3-bromopropene with the following steps. L-cysteine hydrochloride (13 g, 0.083 mol) in $NH_4OH$ (2M, 240 ml) is prepared and pre-cooled to 0 degree C. Then 3-bromopropene (15 g, 0.124 mol) is added to the ice-cooled solution of L-cysteine hydrochloride in $NH_4OH$. The mixture was stirred vigorously at 0 degree C. for 2 h and filtered, and the filtrate was concentrated in vacuum at the temperature less than 40 degree C. to a small volume, and filtered again. The solid was washed repeatedly with ethanol, dried in vacuum, and re-crystallized from 2:3 $H_2O/C_2H_5OH$ to yield purified SAC in white needle crystal appearance. The chemical structure of SAC is determined by Proton Nuclear Magnetic Resonance Spectroscopy.

Example 16

Synthesis of S-ethyl-L-cysteine (SEC)

SEC is synthesized from L-cysteine hydrochloride (1.58 g, 0.01 mol) and ethyl bromide (1.09 g, 0.01 mol) with the following steps. The reaction mixture is diluted with water in a titration manner until a clear solution is formed. No more than necessary amount of water should be added to further dilute the mixture. Ammonia water was added to PH 9.5-10 with stirring at room temperature. After 2 hours reaction, the mixture is acidified with acetic acid to PH 5-5.5. The desired product was cooled in the refrigerator, filtered and washed successively with water and ethyl ether. The chemical structure of SEC is determined by Proton Nuclear Magnetic Resonance Spectroscopy.

Example 17

Synthesis of S-propyl-L-cysteine (SPC)

SPC is synthesized from L-cysteine hydrochloride and propyl bromide with the following steps. L-cysteine hydrochloride (1.58 g, 0.01 mol) in 30 ml of $NH_4OH$ (2M, 240 ml) is prepared and pre-cooled to 0 degree C. Propyl bromide (1.29 g, 0.01 mol) is added to the solution of L-cysteine hydrochloride in 30 ml of $NH_4OH$, and the mixture is stirred at room temperature. The SPC product is then precipitated upon acidification with acetic acid and cooling. The chemical structure of SPC is determined by Proton Nuclear Magnetic Resonance Spectroscopy.

Example 18

Synthesis of S-butyl-L-cysteine (SBC) and S-pentyl-L-cysteine (SPEC)

SBC and SPEC are synthesized from L-cysteine hydrochloride and butyl bromide (for synthesis of SBC) or pentyl bromide (for synthesis of SPEC) with the following steps. L-cysteine hydrochloride (1.58 g) is dissolved in 22.5 ml of 2N sodium hydroxide and 18 ml of ethanol. The mixed solution is stirred and cooled to 25 degree C., butyl bromide (1.45 g, 0.01 mol) (for synthesis of SPEC) or pentyl bromide (2.0 g, 0.01 mol) (for synthesis of SPEC) is added, and the mixture is stirred continuously overnight. Concentrated hydrochloric acid is added to bring the solution to pH 2. Then the mixture is concentrated in vacuum and dried. SBC (or SPEC) is extracted twice with two portions of hot absolute ethanol. The two ethanol extracts are combined, concentrated and dried. Then the dried substance (the product) is re-dissolved in 30 ml of water, and the solution was adjusted to pH 5. The product SBC (or SPEC) is collected, rinsed with cold water, then rinsed with ethanol, and is dried. The chemical structure of SBC (or SPEC) is determined by Proton Nuclear Magnetic Resonance Spectroscopy.

Example 19

Synthesis of S-allylmercapto-L-cysteine (SAMC)

Allicin (5 g) is added to the solution of L-cysteine (2.5 g, 0.207 mol) in $H_2O$ (80 ml) in small portions under vigorous stirring at room temperature. After stirring the mixture at room temperature for 40 min, it is kept at 0 degree C. overnight for reaction. Then the mixture is filtered. The solid product (SAMC) is washed successively with $H_2O$, $C_2H_5OH$, and ethyl acetate until white crystal SAMC is produced.

The foregoing examples illustrate certain exemplary embodiments from which other embodiments, alternatives, variations, and modifications will be apparent to those skilled in the art. Accordingly, the invention is intended to embrace all other such alternatives, modifications, and variations that fall within the spirit and scope of the appended claims.

What is claimed is:

1. A method of treating myocardial infarction by elevating endogenous H2S level in infarcted myocardial cells thereby improving survival rate of the myocardial cells comprising administrating to a subject in injection form with an effective amount of pharmaceutical composition comprising S-propargyl-cysteine (SPRC) that is capable of inducing a measurable cystathionine-γ-lyase (CSE) activity in the myocardial cells, wherein said SPRC is artificially synthesized from cysteine hydrochloride in an aqueous solution, wherein the effective amount of SPRC is at least 50 mg/Kg/day, wherein the subject is suffering from myocardial cell infarction and wherein said SPRC is administered for at least 2 days after the occurrence of the infarction.

2. The method of claim 1 wherein the measurable CSE activity is mediated by up-regulating CSE gene expression in the infarcted myocardial cells induced by SPRC.

3. The method of claim 1 wherein the improved survival rate of the myocardial cells is mediated by down regulating Bax gene expression in the infarcted myocardial cells induced by SPRC.

* * * * *